US012642875B2

(12) United States Patent　　　　(10) Patent No.: US 12,642,875 B2
Ma et al.　　　　　　　　　　　　　　(45) Date of Patent: Jun. 2, 2026

(54) LIPOSOMAL NANOCARRIER DELIVERY SYSTEM FOR TARGETING ACTIVE CD44 MOLECULE, PREPARATION METHOD THEREFOR, AND USES THEREOF

(71) Applicant: Beijing Inno Medicine Co., Ltd., Beijing (CN)

(72) Inventors: Qian Ma, Beijing (CN); Jiefang Sun, Beijing (CN)

(73) Assignee: Beijing Inno Medicine Co., Ltd., Beijing (CN)

( * ) Notice: Subject to any disclaimer, the term of this patent is extended or adjusted under 35 U.S.C. 154(b) by 0 days.

(21) Appl. No.: 16/961,349

(22) PCT Filed: Jan. 21, 2019

(86) PCT No.: PCT/CN2019/072499
§ 371 (c)(1),
(2) Date: Jul. 10, 2020

(87) PCT Pub. No.: WO2019/141271
PCT Pub. Date: Jul. 25, 2019

(65) Prior Publication Data
US 2020/0397926 A1　　Dec. 24, 2020

(30) Foreign Application Priority Data
Jan. 22, 2018　　(CN) ......................... 201810060265.9

(51) Int. Cl.
*A61K 9/00* 　　　(2006.01)
*A61K 49/18* 　　(2006.01)
(Continued)

(52) U.S. Cl.
CPC .......... *A61K 49/1812* (2013.01); *A61K 45/06* (2013.01); *B82Y 5/00* (2013.01)

(58) Field of Classification Search
CPC .................................................. A61K 49/1812
See application file for complete search history.

(56) References Cited

U.S. PATENT DOCUMENTS 8,329,213 B2　　12/2012　Hong et al.
2002/0131995 A1　　9/2002　Szoka et al.
(Continued)

FOREIGN PATENT DOCUMENTS

CN　　　103191411 A　　7/2013
CN　　　104491886 A　　4/2015
(Continued)

OTHER PUBLICATIONS

Avanti Polar Lipids (https://avantilipids.com/tech-support/faqs/suv-vs-luv; accessed Jun. 1, 2023) (Year: 2023).*
(Continued)

*Primary Examiner* — Paul W Dickinson
(74) *Attorney, Agent, or Firm* — Wolf, Greenfield & Sacks, P.C.

(57) ABSTRACT

A liposomal nanocarrier delivery system for targeting an active CD44 molecule, preparation method therefor, and uses thereof. The surface of the liposome is partially modified by a targeting ligand, wherein the targeting ligand is a ligand that can be specifically combined with the active CD44 molecule. The liposomal nanocarrier delivery system can be used for diagnosing, preventing, and treating vulnerable plaque or diseases related to vulnerable plaque.

19 Claims, 17 Drawing Sheets

(51) Int. Cl.
　　 *A61K 45/06* 　　　　(2006.01)
　　 *B82Y 5/00* 　　　　(2011.01)

(56) References Cited

U.S. PATENT DOCUMENTS

| | | | |
|---|---|---|---|
| 2007/0116753 | A1 | 5/2007 | Hong et al. |
| 2008/0026049 | A1 | 1/2008 | Wasan et al. |
| 2010/0119590 | A1 | 5/2010 | Hu et al. |
| 2012/0107229 | A1 | 5/2012 | Huang et al. |
| 2014/0356416 | A1 | 12/2014 | Kesari et al. |
| 2024/0148913 | A1 | 5/2024 | Ma et al. |
| 2024/0424132 | A1 | 12/2024 | Ma et al. |

FOREIGN PATENT DOCUMENTS

| | | | |
|---|---|---|---|
| CN | 105078895 | A | 11/2015 |
| CN | 105163720 | A | 12/2015 |
| CN | 105343895 | A | 2/2016 |
| CN | 105412947 | A | 3/2016 |
| CN | 105664250 | A | 6/2016 |
| CN | 105708800 | A | 6/2016 |
| CN | 105749296 | A | 7/2016 |
| CN | 106362172 | A | 2/2017 |
| CN | 106512023 | A | 3/2017 |
| CN | 106729737 | A | 5/2017 |
| CN | 106798726 | A | 6/2017 |
| CN | 107485603 | A | 12/2017 |
| CN | 110545798 | A | 12/2019 |
| CN | 110974972 | A | 4/2020 |
| CN | 111012924 | A | 4/2020 |
| EP | 3744317 | A1 | 12/2020 |
| JP | H09110722 | A | 4/1997 |
| JP | 2013538829 | A | 10/2013 |
| JP | 2021-523119 | A | 9/2021 |
| KR | 10-2021-0005244 | A | 1/2021 |
| WO | 01/39815 | A2 | 6/2001 |
| WO | WO 2006042146 | A2 | 4/2006 |
| WO | WO 2010/120905 | A2 | 10/2010 |
| WO | WO 2014/121211 | A2 | 8/2014 |
| WO | WO 2019/141271 | A1 | 7/2019 |

OTHER PUBLICATIONS

Peng, Lovastatin Inhibits Cancer Stem Cells and Sensitizes to Chemo- and Photodynamic Therapy in Nasopharyngeal Carcinoma, J Cancer. 2017; 8(9): 1655-1664 (Year: 2017).*

Reichert, Development trends for monoclonal antibody cancer therapeutics, Nature Reviews, vol. 7, May 2007, 349-356 (Year: 2007).*

Iwakuma, Statins and cancer, KU Medicine Magazine, Statins and cancer, Aug. 1, 2017 (Year: 2017).*

Stefanick, A Systematic Analysis of Peptide Linker Length and Liposomal Polyethylene Glycol Coating on Cellular Uptake of Peptide-Targeted Liposomes, ACS Nano, 2013, 7(4), 2935-2947 (Year: 2013).*

Glucksam-Galnoy Yifat et al., Hyaluronan-modified and Regular Multilamellar Liposomes Provide Sub-cellular Targeting to Macrophages, without Eliciting a Pro-Inflammatory Response, *Journal of Controlled Release*, Jun. 16, 2014, pp. 388-393, vol. 160, No. 2.

Liu Lisha et al., Hyaluronic Acid-decorated Reconstituted High Density Lipoprotein Targeting Atherosclerotic Lesions, *Biomaterials, Elsevier, Amsterdam, NL*, Jun. 16, 2014, pp. 8002-8014, vol. 35, No. 27.

Shoshy Mizrahy et al., Hyaluronan-coated Nanoparticles: The Influence of the Molecular Weight on CD44-Hyaluronan Interactions and on the Immune Response, *Journal of Controlled Release, Elsevier, Amsterdam, NL*, Jun. 18, 2011, pp. 231-238, vol. 156, No. 2.

Extended European Search Report for EP19741349, dated Nov. 15, 2021.

International Search Report, PCT/CN2019/072499 [ISA/CN] dated Apr. 18, 2019.

Sharma, A., Liposomes in drug delivery: Progress and limitations, *International Journal of Pharmaceutics*, 154(2), pp. 123-140 (1997).

Arpicco et al., Recent studies on the delivery of hydrophilic drugs in nanoparticulate systems. Journal of Drug Delivery Science and Technology. Apr. 1, 2016;32:298-312.

Beckwitt et al., Lipophilic statins limit cancer cell growth and survival, via involvement of Akt signaling. PLoS One. May 15, 2018;13(5):e0197422. doi: 10.1371/journal.pone.0197422.

Facciorusso et al., Statin Use Decreases the Incidence of Hepatocellular Carcinoma: An Updated Meta-Analysis. Cancers (Basel). Apr. 3, 2020;12(4):874. doi: 10.3390/cancers12040874.

Li et al., Statin and the risk of hepatocellular carcinoma in patients with hepatitis B virus or hepatitis C virus infection: a meta-analysis. BMC Gastroenterol. Apr. 9, 2020;20(1):98. doi: 10.1186/s12876-020-01222-1.

Liu et al., The relationship between statins and breast cancer prognosis varies by statin type and exposure time: a meta-analysis. Breast Cancer Res Treat. Jul. 2017;164(1):1-11. doi: 10.1007/s10549-017-4246-0. Epub Apr. 21, 2017.

Simon et al., Lipophilic Statins and Risk for Hepatocellular Carcinoma and Death in Patients With Chronic Viral Hepatitis: Results From a Nationwide Swedish Population. Ann Intern Med. Sep. 3, 2019;171(5):318-327. doi: 10.7326/M18-2753. Epub Aug. 20, 2019.

[No Author Listed] Crestor (rosuvastatin calcium) Tablets, Astrazeneca, Jan. 2005. Retrieved online: https://www.fda.gov/drugsatfda. 20 pages.

[No Author Listed] Pravachol (pravastatin sodium) Tablets, Bristol-Myers Squibb Company, Dec. 28, 2001. Retrieved online: https://www.fda.gov/drugsatfda. 31 pages.

Jeshycka et al., Voltammetric understanding of ionizable doxorubicin transfer reactions across liquid/liquid interfaces and sensor development. Electrochimica Acta. Aug. 10, 2017;245:211-8. doi: http://dx.doi.org/doi:10.1016/j.electacta.2017.05.096. Author Manuscript, 31 pages.

Li et al., Measurement of drug lipophilicity and pKa using acoustics. Anal Chem. Mar. 20, 2012;84(6):2609-13. doi: 10.1021/ac300087z. Epub Mar. 6, 2012.

Parrales et al., DNAJA1 controls the fate of misfolded mutant p53 through the mevalonate pathway. Nat Cell Biol. Nov. 2016;18(11):1233-1243. doi: 10.1038/ncb3427. Epub Oct. 24, 2016. Author Manuscript, 24 pages.

U.S. Appl. No. 19/030,462, filed Jan. 17, 2025, Ma et al.

U.S. Appl. No. 19/030,601, filed Jan. 17, 2025, Ma et al.

U.S. Appl. No. 18/689,166, filed Mar. 5, 2024, Ma et al.

[No Author Listed] National Center for Cardiovascular Diseases, China. Report on cardiovascular diseases in China 2018. Beijing, China: Encyclopedia of China Publishing House, 242 pages.

Ahmadi et al., Effects of statins on the chemoresistance-The antagonistic drug-drug interactions versus the anti-cancer effects. Biomed Pharmacother. Dec. 2018;108:1856-1865. doi: 10.1016/j.biopha.2018.09.122. Epub Oct. 23, 2018.

Akbarzadeh et al., Liposome: classification, preparation, and applications. Nanoscale Res Lett. Feb. 22, 2013;8(1):102. doi: 10.1186/1556-276X-8-102.

Aksoy et al., Comparison of the Effects of Statins on A549 Nonsmall-Cell Lung Cancer Cell Line Lipids Using Fourier Transform Infrared Spectroscopy: Rosuvastatin Stands Out. Lipids. May 2021;56(3):289-299. doi: 10.1002/lipd.12296. Epub Feb. 21, 2021.

Belousov et al., Clinical Pharmacokinetics. Dosing practice. Moscow: Litterra, 2005. 288 pages.

Hu et al., Application and prospect of the nano metal-organic frameworks in medicine 纳米金 属有机框架 载药系统的应 用与展望 Northwest Journal of Pharmacy, Mar. 30, 2015, p. 220. doi:10.3969/j.issn.1004-2407.2015.02.037.

Kashkin et al., Expression profiling and putative mechanisms of resistance to doxorubicin of human lung cancer cells. Dokl Biochem Biophys. Jan.-Feb. 2010;430:20-3. doi: 10.1134/s1607672910010072.

Kummerer, Pharmaceuticals in the environment. Annual review of environment and resources. Nov. 21, 2010;35(1):57-75. doi: 10.1146/annurev-environ-052809-161223.

(56)          References Cited

OTHER PUBLICATIONS

Levine et al., Drosophila Lung Cancer Models Identify Trametinib plus Statin as Candidate Therapeutic. Cell Rep. Feb. 16, 2016;14(6):1477-1487. doi: 10.1016/j.celrep.2015.12.105. Epub Jan. 28, 2016. Author Manuscript, 23 pages.

Ma et al., The Current Research Status of CD44 Molecule (CD44 在靶向给药中) Int J Respir, 2006;26(12)938.

Paliwal et al., Hyaluronic acid modified pH-sensitive liposomes for targeted intracellular delivery of doxorubicin. J Liposome Res. Dec. 2016;26(4):276-87. doi: 10.3109/08982104.2015.1117489. Epub Jan. 19, 2016.

Peng et al., Application of dendrimer in targeted drug delivery: recent progress (树枝状聚合物 在靶向给药中 的应用进展 Academic Journal of Second Military Medical University, Jan. 2011, vol. 32, p. 96-100.

Pitarresi et al., Self-assembled amphiphilic hyaluronic acid graft copolymers for targeted release of antitumoral drug. J Drug Target. May 2010;18(4):264-76. doi: 10.3109/10611860903434027. (Abstract).

Wang et al., Application of Hydroxyapatite Nanoparticle as Drug Carrier (纳米羟基磷灰石在 药物载体中的应用),Fine and Specialty Chemicals, Jan. 6, 2006, vol. 14, p. 9.

Yadav et al., Preparation and characterization of HA-PEG-PCL intelligent core-corona nanoparticles for delivery of doxorubicin. J Drug Target. Jul. 2008;16(6):464-78. doi: 10.1080/10611860802095494.

Zhang et al., Preparation of Hyaluronic Acid-Masked Metal-Organic Frameworks and Their Study on Drug Loading for Chemotherapy (透明质酸遮蔽金 属有机框架的 制备及其担载化疗 药物的研究), Chinese Chemical Society 2017 National Polymer Academic Paper Conference, Oct. 10, 2017. (Abstract).

Kones, Rosuvastatin, inflammation, C-reactive protein, JUPITER, and primary prevention of cardiovascular disease—a perspective. Drug Des Devel Ther. Dec. 9, 2010;4:383-413. doi: 10.2147/DDDT. S10812.

Office Action for Application No. KR10-2024-7009375, dated Nov. 20, 2025.

Restriction Requirement for Application No. U.S. Appl. No. 18/689,166, dated Nov. 17, 2025.

Falk, Pathogenesis of atherosclerosis. J Am Coll Cardiol. Apr. 18, 2006;47(8 Suppl):C7-12. doi: 10.1016/j.jacc.2005.09.068.

Gao et al., Monodispersed mesoporous silica nanoparticles with very large pores for enhanced adsorption and release of DNA. J Phys Chem B. Feb. 12, 2009;113(6):1796-804. doi: 10.1021/jp807956r.

Hashizume et al., Stable vesicular nanoparticle 'Cerasome'as an organic-inorganic hybrid formed with organoalkoxysilane lipids having a hydrogen-bonding unit. Thin Solid Films. Aug. 22, 2003;438:20-6.

Hiatt et al., Atherosclerotic Peripheral Vascular Disease Symposium II: nomenclature for vascular diseases. Circulation. Dec. 16, 2008;118(25):2826-9. doi: 10.1161/CIRCULATIONAHA.108. 191171. Erratum in: Circulation. Jun. 30, 2009;119(25):e604.

Katagiri et al., Layered paving of vesicular nanoparticles formed with cerasome as a bioinspired organic-inorganic hybrid. J Am Chem Soc. Jul. 10, 2002;124(27):7892-3. doi: 10.1021/ja0259281.

Li et al., Drug nanocrystallisation within liposomes. J Control Release. Oct. 2, 20188;288:96-110. doi: 10.1016/j.jconrel.2018.09. 001. Epub Sep. 2, 2018.

Muller et al., Circadian variation and triggers of onset of acute cardiovascular disease. Circulation. Apr. 1989;79(4):733-43. doi: 10.1161/01.cir.79.4.733.

Naghavi et al., New developments in the detection of vulnerable plaque. Curr Atheroscler Rep. Mar. 2001;3(2):125-35. doi: 10.1007/ s11883-001-0048-1.

Nasr et al., Effective atherosclerotic plaque inflammation inhibition with targeted drug delivery by hyaluronan conjugated atorvastatin nanoparticles. May 7, 2020;12(17):9541-9556. doi: 10.1039/ d0nr00308e. Author Manuscript, 32 pages.

Reiner, Pathophysiology and Classification of Cardiovascular Diseases Caused by Atherosclerosis. EJIFCC. Jul. 3, 2003;14(2):44-46.

Sasaki et al., Cerasome as an infusible and cell-friendly gene carrier: synthesis of cerasome- forming lipids and transfection using cerasome. Nat Protoc. 2006;1(3):1227-34. doi: 10.1038/nprot.2006.182.

Takayama et al., Comparison of the Effect of Rosuvastatin 2.5 mg vs 20 mg on Coronary Plaque Determined by Angioscopy and Intravascular Ultrasound in Japanese With Stable Angina Pectoris (from the Aggressive Lipid-Lowering Treatment Approach Using Intensive Rosuvastatin for Vulnerable Coronary Artery Plaque [ALTAIR] Randomized Trial). Am J Cardiol. Apr. 1, 20165;117(8):1206-12. doi: 10.1016/j.amjcard.2016.01.013. Epub Jan. 2, 20168.

Thim et al., From vulnerable plaque to atherothrombosis. J Intern Med. May 2008;263(5):506-16. doi: 10.1111/j.1365-2796.2008. 01947.x.

Zhao et al., Smart nanocarrier based on PEGylated hyaluronic acid for deacetyl mycoepoxydience: High stability with enhanced bioavailability and efficiency. Carbohydr Polym. Jan. 1, 2019;203:356-368. doi: 10.1016/j.carbpol.2018.09.071. Epub Sep. 29, 2018.

* cited by examiner (a)

(b)

LP1-(Fe3O4/DXMS)- HI44a. LP1-(Fe₃O₄/IL-10) - HI44a

Percentage of plaque progression %

LP1-(Asp/Clo)-Col

LIPOSOMAL NANOCARRIER DELIVERY SYSTEM FOR TARGETING ACTIVE CD44 MOLECULE, PREPARATION METHOD THEREFOR, AND USES THEREOF

CROSS-REFERENCES TO RELATED APPLICATIONS

This application claims priority to and is the National Stage of International Application No. PCT/CN2019/072499, filed on Jan. 21, 2019, and further claims priority to Chinese Patent No. CN201810060265.9, filed on Jan. 22, 2018, the content of each of which are incorporated herein by reference.

TECHNICAL FIELD

The present invention belongs to the technical field of targeted drug delivery, and in particular relates to a nanocarrier for targeting an activated CD44 molecule, especially for targeting a vulnerable plaque and especially it's a liposome nanocarrier delivery system. The present invention further relates to a preparation method and the use of the nanocarrier especially the liposome delivery system, particularly in the diagnosis, prevention and treatment of a vulnerable plaque or a disease associated with the vulnerable plaque.

BACKGROUND OF THE INVENTION

At present, acute cardiovascular events, mainly including acute myocardial infarction and sudden cardiac death, have become the number one threat for human health. According to statistics, about 20 million people die from acute cardiovascular events worldwide each year. The situation in China is also not optimistic. More than 700,000 people die from acute myocardial infarction and sudden cardiac death each year, which has become one of the most notable diseases that seriously threaten the health of the Chinese people. Studies have shown that most of the acute myocardial infarction and sudden cardiac death are caused by atherosclerotic plaques. Since the 1970s, the process and mechanism in which a chronic atherosclerotic plaque leads to acute coronary syndrome (ACS) and stroke have been explored constantly.

In 1989, Muller and colleagues (Circadian Variation and Triggers of Onset of Acute Cardiovascular Disease. Circulation. 1989; 79(4): 733-43) proposed the concept of "vulnerable plaque", presuming that such a plaque is the fundamental cause of most of the acute cardiovascular and cerebrovascular events. A vulnerable plaque (also known as "unstable plaque") refers to an atherosclerotic plaque that tends to form thrombus or is likely to progress rapidly into "criminal plaque", including rupture-prone plaque, erosion-prone plaque and partially calcified nodular lesions. A large number of studies have shown that most of the acute myocardial infarction and stroke are caused by the rupture of vulnerable plaques having mild to moderate stenosis, followed by thrombosis. Naghavi and colleagues (New Developments in the Detection of Vulnerable plaque. Curr Atheroscler Rep. 2001; 3(2): 125-35) et al. provided the histological definition and criteria for the vulnerable plaque. The main criteria include active inflammation, thin fibrous caps and large lipid cores, endothelial exfoliation together with platelet aggregation on the surface, plaque fissures or lesions, and severe stenosis. Secondary criteria include calcified plaques on the surface, yellow and lustrous plaques, intraplaque hemorrhage, and positive remodeling.

Therefore, early intervention is critical for the vulnerable plaque. However, as the degree of vascular stenosis caused by the vulnerable plaque is normally not so high that many patients have no prodromal symptoms, the early diagnosis of the vulnerable plaque in clinical is very difficult, making the vulnerable plaque extremely dangerous. Therefore, an urgent problem to be solved in the prevention and treatment of acute myocardial infarction is how to accurately identify and diagnose a vulnerable plaque as early as possible, so that an effective intervention can be carried out.

Currently, the commonly used techniques for the diagnosis of a vulnerable plaque mainly include coronary angiography, intravascular ultrasound (IVUS), optical coherence tomography (OCT), etc., but these techniques are all invasive examination with low diagnostic resolution and accuracy, and high expenses, which limits the clinical use of these techniques to some extent. Therefore, currently, there is an urgent need for non-invasive diagnostic techniques and preparations for the vulnerable plaque.

In addition, the current method of treating a vulnerable plaque is mainly via systemic administration, such as oral administration of statins (hydroxymethyl glutaryl coenzyme A (HMG-CoA) reductase inhibitors), aspirin, matrix metalloproteinases (MMPs) inhibitors and/or fibrates, etc. These drugs act to stabilize plaques by reducing lipids in plaques, improving vascular remodeling, etc through regulating systemic blood fats, fighting inflammation, inhibiting proteases and platelet production, etc. However, in clinical applications, it has been found that the therapeutic effects of current drugs for treating vulnerable plaques are not satisfactory. For example, the statins commonly used in clinical practice have relatively low bioavailability when administered orally, such as <5% for simvastatin, about 12% for atorvastatin, and about 20% for rosuvastatin. Animal experiments have also confirmed that only when the dose of statins is increased to more than 1 mg/kg can they increase the thickness of the fibrous cap and reduce the volume of plaques, which makes the stability of oral administration of statins and their effect of reversing plaques encounter a bottleneck. At present, clinical trials have also confirmed that the treatment of vulnerable plaques by oral administration of statins requires intensive large doses to stabilize the vulnerable plaques, while treatment with systemic large doses of statins also has a risk of increased incidence of serious side effects (such as abnormal liver function, rhabdomyolysis, type II diabetes, etc.).

For existing systemic administration, usually only a very small portion of active ingredients can actually act on a lesion site after a drug enters the body. This is the fundamental cause that limits the efficacy of the drug and produces toxic side effects. A targeted drug delivery system refers to a drug delivery system that has the ability of targeted drug delivery. After administered via a certain route, the drug contained in the targeted drug delivery system is specifically enriched in a targeted site by a carrier with a targeting probe. The targeted drug delivery system is capable of making the drug targeting to a particular lesion site and releasing the active ingredients at the target lesion site. Therefore, the targeted drug delivery system may result in a relatively high concentration of the drug in the target lesion site, and a reduced dose of the drug in the blood circulation, thereby improving the drug effect while suppressing toxic side effects, and reducing damage to normal tissues and cells.

In the field of diagnosis and treatment of vulnerable plaques, there are also some techniques for diagnosing the vulnerable plaques by modifying the nanocarriers with targeting ligands. However, a major problem of such targeting probes, which target vulnerable plaques, in clinical practice is the insufficient specificity of these preparations to targeted sites. For example, for most of such preparations, macrophages are selected as the targeted sites; however, since macrophages are present throughout the body, the targeting specificity of the probes is not satisfactory. Therefore, the difficulty in the development of targeting preparations which target vulnerable plaques lies in the discovery of targeted sites with significant targeting specificity in cells within the vulnerable plaques.

CD44 is a type of adhesive molecules that are widely distributed on the surface of lymphocytes, monocytes, endothelial cells, etc. The main ligand of the CD44 molecule is hyaluronic acid (abbreviated as "HA"). Based on the activation state of cells expressing CD44, CD44 can exist in a relatively static state (which cannot bind to HA), an induced activation state (which can bind to HA after activation), and a structurally active state (which can bind to HA without activation), while CD44 on the surface of most normal cells are in the relatively static state and cannot bind to HA.

A number of previous studies have shown that CD44 is not an ideal targeted sites with significant targeting specificity. This is because CD44 is widely distributed in the human body, especially on the surface of organs rich in reticuloendothelial. Therefore, the following problem will be encountered in the development of the targeted drug delivery system using CD44 as the targeted sites: if the CD44 on the surface of targeted cells has insufficient affinity to HA to provide significant specificity, such a targeted drug delivery system will not have specifically targeting properties.

Therefore, finding specific targeted sites present at vulnerable plaques and targeted drug delivery systems suitable for targeting vulnerable plaques, thereby developing a targeted drug delivery system capable of specifically targeting vulnerable plaques while achieving stable and sustained release of the drug, has become an urgent technical problem to be solved in the medical field.

To date, there is no report on the expression status of CD44 on the surface of macrophages, monocytes, endothelial cells, lymphocytes and smooth muscle cells mainly present within vulnerable plaques or on their affinity for HA, and there is no any prior art regarding designing a targeted drug delivery system for diagnosing or treating the vulnerable plaques or a disease associated with the vulnerable plaques while achieving stable and sustained release of the drug by utilizing the interaction between HA and CD44 and the specific microenvironment of the vulnerable plaques either.

SUMMARY OF THE INVENTION

(1) Overview of the Invention

The present inventors have found that as compared to normal cells, CD44 on the surface of cells, such as endothelial cells, macrophages, and smooth muscle cells, in vulnerable plaques is activated by the specific microenvironment (such as inflammatory factors) of the vulnerable plaques, and therefore their binding ability to HA is suddenly increased by dozens of times. This finding suggests that a large number of activated CD44 molecules present on the surface of cells at vulnerable plaques provide ideal targeted sites for the targeted drug delivery system with HA as a targeting ligand. To this end, the present invention provides a targeted drug delivery system for specifically targeting an activated CD44 molecule, especially for targeting a vulnerable plaque.

The present inventors have also discovered that loading with a CD44 activator can promote the further activation of CD44 on the surface of the lesion cells, and can amplify the targeting affinity of CD44 for HA in a short time, which significantly increases the concentration of targeting compositions bound to the cell surface, showing active significance for the tracer diagnosis and treatment of vulnerable plaques. To this end, the targeted drug delivery system of the present invention can be simultaneously loaded with a CD44 activator, which can significantly increase the concentration of a tracer or therapeutic agent compound in a short period of time to improve diagnostic sensitivity or therapeutic effect.

The present inventors have also found that in vulnerable plaques, along with the high level of activation and over expression of CD44, the endogenous macromolecular HA is generated in a large quantity by stimulation, which binds to CD44 on the cell surface, promoting aggregation of cells such as macrophages and lymphocytes in the vulnerable plaques. Such an endogenous HA, which binds to CD44 on a cell surface, can form a barrier to drug entry and reduce the bioavailability of the drug. To this end, the targeted drug delivery system of the present invention can be loaded with a small-molecular hyaluronic acid or a hyaluronic acid derivative capable of specifically binding to a CD44 molecule on a cell surface at the vulnerable plaque, which eliminates the barrier formed by the endogenous HA on the cell surface by competing the binding of the endogenous HA on the cell surface, facilitating the successful intracellular release of the drug in the lesion cells and providing a significant therapeutic effect.

In summary, the present invention relates to the following aspects:

The present invention provides a liposome nanocarrier delivery system for targeting an activated CD44 molecule.

The present invention provides a liposome nanocarrier delivery system for targeting a vulnerable plaque.

The present invention provides a method for preparing the liposome nanocarrier delivery system of the present invention for targeting a vulnerable plaque.

The present invention further provides a medicament, comprising the nanocarrier delivery system of the present invention for targeting a vulnerable plaque and pharmaceutically acceptable carriers.

The present invention further provides a diagnostic preparation, comprising the nanocarrier delivery system of the present invention for targeting a vulnerable plaque.

The present invention further provides the use of the nanocarrier delivery system of the present invention for targeting a vulnerable plaque in the preparation of a medicament for preventing and/or treating the vulnerable plaque or a disease associated with the vulnerable plaque.

The present invention further provides the use of the nanocarrier delivery system of the present invention for targeting a vulnerable plaque in the preparation of a diagnostic preparation for diagnosing the vulnerable plaque or a disease associated with the vulnerable plaque.

The present invention further provides a method for preventing and/or treating the vulnerable plaque or a disease associated with the vulnerable plaque, wherein the method comprises administering the nanocarrier delivery system of the present invention for targeting a vulnerable plaque to a subject in need thereof.

The present invention further provides a method for diagnosing the vulnerable plaque or a disease associated with the vulnerable plaque, wherein the method comprises administering the nanocarrier delivery system of the present invention for targeting a vulnerable plaque to a subject in need thereof.

Specific embodiments of the technical solutions of the present invention and their meanings will be described in detail below.

(2) Technical Terms and Meanings Thereof

The terms mentioned herein have the following meanings:

The "vulnerable plaque" (also known as an "unstable plaque") refers to an atherosclerotic plaque that tends to form thrombus or is likely to progress rapidly into "criminal plaque", including rupture-prone plaque, erosion-prone plaque and partially calcified nodular lesions. A large number of studies have shown that most of the acute myocardial infarction and stroke are caused by the rupture of vulnerable plaques with mild to moderate stenosis, followed by thrombosis. Histological manifestations of the vulnerable plaque include active inflammation, thin fibrous caps and large lipid cores, endothelial exfoliation with surface platelet aggregation, plaque fissures or lesions, and severe stenosis, as well as calcified plaques on the surface, yellow and lustrous plaques, intraplaque hemorrhage, and positive remodeling.

The "disease associated with the vulnerable plaque" mainly refers to a disease associated with the "vulnerable plaque", characterized by the "vulnerable plaque", caused by the "vulnerable plaque" or secondary to the "vulnerable plaque" during the occurrence and development of the disease. The "disease associated with the vulnerable plaque" mainly includes atherosclerosis, coronary atherosclerotic heart disease (including acute coronary syndrome, asymptomatic myocardial ischemia—latent coronary heart disease, angina pectoris, myocardial infarction, ischemic heart disease, sudden death, and in-stent restenosis), cerebral arteriosclerosis (including stroke), peripheral vascular atherosclerosis (including peripheral arterial occlusive disease, arteriosclerosis of retina, carotid atherosclerosis, renal atherosclerosis, lower extremity atherosclerosis, upper extremity atherosclerosis and atherosclerotic impotence), aortic dissection, hemangioma, thromboembolism, heart failure, cardiogenic shock, etc.

The "targeted drug delivery system" refers to a drug delivery system that has the ability of targeted drug delivery. After administration via a certain route, the drug contained in the targeted drug delivery system is specifically enriched in the targeted site by the action of a special carrier or a targeting warhead (e.g., a targeting ligand). Currently known means for achieving targeted drug delivery include utilizing the passive targeting properties of various microparticle delivery systems, introducing chemical modification on the surface of microparticle delivery systems, utilizing some special physical and chemical properties, utilizing an antibody-mediated targeted drug delivery, utilizing a ligand-mediated targeted drug delivery, utilizing a prodrug targeted drug delivery, etc. Among others, the ligand-mediated targeted drug delivery combines a drug carrier with a ligand, which utilizes the characteristic that a specific receptor in certain organ and tissue specifically binds to its specific ligand, thereby directing the drug to a specific target tissue.

"Liposome carrier" is a lipid-like bilayer drug carrier, which encapsulates drugs in lipid bilayer to form microvesicles. It can also be lipid bicelle structure, which is generally a disk vesicle formed by self-assembly of long chain phospholipids and short chain phospholipids or surfactants. Long chain phospholipids form the plane of the disk, and short chain phospholipids surround the side edges of the disk. 1,2-dimyristoyl-sn-glycero-3-phospho-choline (DMPC) is often used as a long chain phospholipid component, and the surface charge of bicelle can be changed and its versatility can be realized by doping other phospholipid components with the same chain length but with different head groups. And short chain phospholipids form a high curvature region to reduce the edge energy of aggregates to stabilize the bicelle.

The "hyaluronic acid (abbreviated as "HA")" is a polymer of a macromolecule and has the formula of $(C_{14}H_{21}NO_{11})_n$. It is a higher polysaccharide consisting of the units D-glucuronic acid and N-acetylglucosamine. D-glucuronic acids and N-acetylglucosamines are linked by $\beta$-1,3-glycosidic bonds, and the disaccharide units are linked by $\beta$-1,4-glycosidic bonds. Thanks to a unique molecular structure and physical and chemical property, the hyaluronic acid displays various important physiological functions in an organism, such as lubricating joints, regulating the permeability of blood vessel walls, regulating the diffusion and transportation of proteins, water, and electrolytes, and promoting wound healing. It is especially important that the hyaluronic acid has a special water retention effect and is the substance having the best moisture retention property found in nature.

The "derivative of the hyaluronic acid" as used herein refers to any derivative of the hyaluronic acid capable of retaining the ability of the hyaluronic acid for specifically binding to CD44 molecules on the surface of cells at vulnerable plaques, including, but not limited to, pharmaceutically acceptable salts of the hyaluronic acid, lower alkyl (alkyl containing 1 to 6 carbon atoms) esters, prodrugs capable of forming the hyaluronic acid by hydrolysis or other means in the body, etc. Judging whether a substance is a "derivative of the hyaluronic acid" can be achieved by measuring the ability of the substance for specifically binding to CD44 molecules on the cell surface at vulnerable plaques, which is within the skills of a person skilled in the art.

The "CD44 molecule" is a type of transmembrane proteoglycan adhesion molecules widely expressed on the cell membrane of cells such as lymphocytes, monocytes, and endothelial cells, consisting of three segments, i.e., an extracellular segment, a transmembrane segment, and an intracellular segment. The CD44 molecule can mediate a variety of interactions between cells and cells, and between cells and extracellular matrix, participate in the transmission of various signals in the body, and thus change the biological function of cells. The primary ligand for the CD44 molecule is hyaluronic acid, and the receptor-ligand binding of the CD44 molecule and the hyaluronic acid determines the adhesion and/or migration of cells in the extracellular matrix. In addition, the CD44 molecule is also involved in the metabolism of the hyaluronic acid.

"About" represents a set of all values within the range of ±5% of the numerical value given thereafter.

(3) Detailed Description of the Invention

The first aspect of the present invention provides a liposome nanocarrier delivery system for targeting activated CD44 molecules, the surface of the nanocarrier is partially modified by a targeting ligand, and the targeting ligand is a ligand capable of specifically binding to the activated CD44 molecule.

The second aspect of the present invention provides a liposome nanocarrier delivery system for targeting vulnerable plaques, the surface of the nanocarrier is partially modified by a targeting ligand, and the targeting ligand is a ligand capable of specifically binding to a CD44 molecule on a cell surface at the vulnerable plaque. Other modifications can be made to the surface of the nanocarrier to achieve better results. Modification of PEG on the surface of the carrier can achieve a long circulation effect and prolong the half-life of the drug. Modification of membrane penetrating peptide, self peptide SEP, or simultaneous modification of double ligands on the surface of the carrier can all play a role in amplifying the drug effect.

According to the nanocarrier delivery system of the first or the second aspect, wherein the liposome carrier is selected from bicelle, small unilamellar vesicles, large unilamellar vesicles and multilamellar vesicles. "Liposome carrier" is a lipid bilayer drug carrier, which encapsulates drugs in lipid bilayer or hydrophilic lumen to form microvesicles or disk structure.

The structure of bicelle may be generally a disk vesicle formed by self-assembly of long chain phospholipids and short chain phospholipids or surfactants. Long chain phospholipids form the plane of the disk, and short chain phospholipids surround the side edges of the disk. 1,2-dimyristoyl-sn-glycero-3-phospho-choline (DMPC) is often used as a long chain phospholipid component, and the surface charge of bicelle can be changed and its versatility can be realized by doping other phospholipid components with the same chain length but with different head groups. And short chain phospholipids which is often selected as 1,2-di-n-heptadecanoyl phosphatidylcholine form a high curvature region to reduce the edge energy of aggregates to stabilize the bicelle.

According to the nanocarrier delivery system of the first or the second aspect, wherein the targeting ligand is selected from GAG, collagen, laminin, fibronectin, selectin, osteopontin (OPN), and monoclonal antibodies HI44a, HI313, A3D8, H90 and IM7, or is selected from a hyaluronic acid or a hyaluronic acid derivative capable of specifically binding to a CD44 molecule on a cell surface at the vulnerable plaque.

According to the nanocarrier delivery system of the first or the second aspect, wherein the nanocarrier is loaded with a substance for diagnosing, preventing and/or treating a disease associated with the presence of CD44 molecule activation.

According to the liposome nanocarrier delivery system of the first or the second aspect, wherein the nanocarrier is loaded with a substance for diagnosing, preventing, and/or treating the vulnerable plaque or a disease associated with the vulnerable plaque.

In an embodiment, the substance is a substance for diagnosing the vulnerable plaque or a disease associated with the vulnerable plaque.

In an embodiment, the substance for diagnosing the vulnerable plaque or a disease associated with the vulnerable plaque is a tracer.

In an embodiment, the tracer is selected from a CT tracer, an MRI tracer and a radioisotopic tracer.

In an embodiment, the CT tracer is selected from an iodine-based nanoscale contrast agent, gold-based nanoscale contrast agent, tantalum oxide-based nanoscale contrast agent, bismuth-based nanoscale contrast agent, lanthanide-based nanoscale contrast agent, or other tracers with a similar structure; more preferably, the CT tracer is selected from iodinated contrast agent or nanogold, or other tracers with a similar structure; further preferably, the CT tracer is selected from iohexol, iocarmic acid, ioversol, iodixanol, iopromide, iobitridol, iomeprol, iopamidol, ioxilan, acetrizoic acid, iodipamide, iobenzamic acid, ioglycamic acid, diatrizoic acid, sodium iotalamate, pantopaque, iopanoic acid, iodoalphionic acid, sodium acetrizoate, sodium iodomethamate, propyliodone, diodone, iotrolan, iopydol, endografin, iotalamic acid, meglumine diatrizoate, metrizoic acid, metrizamide, iodinated oil or ethiodized oil, or other tracers with a similar structure; preferably, the CT tracer is nanogold; and/or the MRI tracer is selected from a longitudinal relaxation contrast agent and a transverse relaxation contrast agent; more preferably, the MRI tracer is selected from a paramagnetic contrast agent, a ferromagnetic contrast agent and a superparamagnetic contrast agent; further preferably, the MRI tracer is selected from Gd-DTPA and the linear, cyclic polyamine polycarboxylate chelate and manganese porphyrin chelate thereof, macromolecular gadolinium chelate, biomacromolecule-modified gadolinium chelate, folic acid-modified gadolinium chelate, dendrimer contrast agent, liposome-modified contrast agent and gadolinium-containing fullerene, or other tracers with a similar structure; and preferably, the MRI tracer is selected from gadopentetate dimeglumine, gadoterate meglumine, gadobenate dimeglumine, gadodiamide, ferric ammonium citrate effervescent granules, paramagnetic iron oxide (Fe3O4 NPs), or other tracers with a similar structure; preferably, the MRI tracer is Fe3O4 NPs;

the radioisotopic tracer is selected from fludeoxyglucose labeled by carbon 14 (14C), carbon 13 (13C), phosphorus 32 (32P), sulfur 35 (35S), iodine 131 (131I), hydrogen 3 (3H), technetium 99 (99Tc) and fluorine 18 (18F); preferably the radioisotopic tracer is fluorine 18-labeled fludeoxyglucose.

In an embodiment, the substance is one or more of a drug, polypeptide, nucleic acid and cytokine for diagnosing, preventing, and/or treating the vulnerable plaque or a disease associated with the vulnerable plaque.

In an embodiment, the substance is a CD44 activator.

In an embodiment, the CD44 activator is a CD44 antibody mAb, IL5, IL12, IL18, TNF-α, LPS.

In an embodiment, the substance is a small-molecular hyaluronic acid or a hyaluronic acid derivative capable of specifically binding to a CD44 molecule on a cell surface at the vulnerable plaque;

preferably, the small-molecular hyaluronic acid or the hyaluronic acid derivative capable of specifically binding to a CD44 molecule on a cell surface at the vulnerable plaque has a molecular weight in the range of 1-500 KDa, preferably 1-20 KDa, more preferably 2-10 KD.

In an embodiment, the nanocarrier is loaded with a substance for diagnosing, preventing, and/or treating the vulnerable plaque or a disease associated with the vulnerable plaque and a CD44 activator concurrently;

preferably, the nanocarrier is loaded with a substance for preventing and/or treating the vulnerable plaque or a disease associated with the vulnerable plaque, and a small-molecular hyaluronic acid or a hyaluronic acid derivative capable of specifically binding to a CD44 molecule on a cell surface at the vulnerable plaque concurrently;

more preferably, the nanocarrier is loaded with a substance for diagnosing the vulnerable plaque or a disease associated with the vulnerable plaque, a substance for preventing and/or treating the vulnerable plaque or a disease associated with the vulnerable plaque, optionally, a CD44 activator, and optionally, a small-molecular hyaluronic acid or a hyaluronic acid derivative capable of specifically binding to a CD44 molecule on a cell surface at the vulnerable plaque concurrently.

In an embodiment, the substance is a substance for preventing and/or treating the vulnerable plaque or a disease associated with the vulnerable plaque;

preferably, the substance for preventing and/or treating the vulnerable plaque or a disease associated with the vulnerable plaque is one or more selected from the group consisting of statins, fibrates, antiplatelet drugs, PCSK9 inhibitors, anticoagulant drugs, angiotensin converting enzyme inhibitors (ACEI), calcium ion antagonists, MMPs inhibitors, $\beta$ receptor blockers, glucocorticoid or other anti-inflammatory substances such as IL-1 antibody canakinumab, and the pharmaceutically acceptable salts thereof, including active preparation of the drugs or substances above, and endogenous anti-inflammatory cytokines such as interleukin 10 (IL-10);

more preferably, the substance for preventing and/or treating the vulnerable plaque or a disease associated with the vulnerable plaque is one or more selected from the group consisting of lovastatin, atorvastatin, rosuvastatin, simvastatin, fluvastatin, pitavastatin, pravastatin, bezafibrate, ciprofibrate, clofibrate, gemfibrozil, fenofibrate, probucol, anti-PCSK9 antibodies such as evolocumab, alirocumab, bococizumab, RG7652, LY3015014 and LGT-209, or adnectin such as BMS-962476, antisense RNAi oligonucleotides such as ALN-PCSsc, nucleic acids such as microRNA-33a, microRNA-27a/b, microRNA-106b, microRNA-302, microRNA-758, microRNA-10b, microRNA-19b, microRNA-26, microRNA-93, microRNA-128-2, microRNA-144, microRNA-145 antisense strands and the nucleic acid analogs thereof such as locked nucleic acids, aspirin, acemetacin, troxerutin, dipyridamole, cilostazol, ticlopidine hydrochloride, sodium ozagrel, clopidogrel, prasugrel, cilostazol, beraprost sodium, ticagrelor, cangrelor, tirofiban, eptifibatide, abciximab, unfractionated heparin, clexane, fraxiparine, fondaparinux sodium, warfarin, dabigatran, rivaroxaban, apixaban, edoxaban, bivalirudin, enoxaparin, tedelparin, ardeparin, bishydroxycoumarin, nitrate coumarin, sodium citrate, hirudin, argatroban, benazepril, captopril, enalapril, perindopril, fosinopril, lisinopril, moexipril, cilazapril, perindopril, quinapril, ramipril, trandolapril, candesartan, eprosartan, irbesartan, losartan, telmisartan, valsartan, olmesartan, tasosartan, nifedipine, nicardipine, nitrendipine, amlodipine, nimodipine, nisoldipine, nilvadipine, isradipine, felodipine, lacidipine, diltiazem, verapamil, chlorhexidine, minocycline, MMI-166, metoprolol, atenolol, bisoprolol, propranolol, carvedilol, batimastat, marimastat, prinomastat, BMS-279251, BAY 12-9566, TAA211, AAJ996A, nacetrapib, evacetrapib, Torcetrapib, Dalcetrapib, prednisone, methylprednisolone, betamethasone, beclomethasone dipropionate, diprospan, prednisolone, hydrocortisone, dexamethasone or other anti-inflammatory substances such as IL-1 antibody canakinumab, and the effective fragments or pharmaceutically acceptable salts thereof, and one or more of the pharmaceutically acceptable salts, including active structure fragments of the substances above, and endogenous anti-inflammatory cytokines such as interleukin 10 (IL-10).

The third aspect of the present invention provides a method for the preparation of a nano-delivery system for targeting vulnerable plaques according to the first aspect or the second aspect, the method comprises the steps of:

(1) dissolving an appropriate amount of phospholipid molecules in suitable organic solvent, preparing the liposome nanocarrier by a film hydration method, wherein for a less polar drug molecule, it is necessary to form film together with the phospholipid molecule in this step;

(2) optionally, an aqueous medium optionally containing a water-soluble substance for diagnosing, preventing and/or treating the vulnerable plaque or a disease associated with the vulnerable plaque is added to the nanocarrier delivery system obtained in step (1) to form crude suspension;

(3) dissolving the targeting ligand in suitable buffer solution solvent, and adding the carrier molecule obtained in step (2) to the targeting ligand solution for reaction, to obtain the nanocarrier delivery system;

(4) optionally removing the unloaded substances for diagnosing, preventing and/or treating the vulnerable plaque or a disease associated with the vulnerable plaque contained in the crude suspension obtained in step (3) by dialysis to obtain the loaded nano delivery system.

The forth aspect of the present invention provides a medicament, the medicament comprising the nanocarrier delivery system according to the first aspect or the second aspect and pharmaceutically acceptable carriers.

The fifth aspect of the present invention provides a diagnostic preparation, the diagnostic preparation comprises the nanocarrier delivery system according to the first aspect or the second aspect.

The sixth aspect of the present invention provides the use of the nanocarrier delivery system according to the first aspect or the second aspect, the medicament according to the forth aspect, or the diagnostic preparation according to the fifth aspect in the preparation for preventing and/or treating a disease associated with the presence of CD44 molecule activation.

The seventh aspect of the present invention provides the use of the nanocarrier delivery system according to the first aspect or the second aspect, the medicament according to the forth aspect, or the diagnostic preparation according to the fifth aspect in the preparation for preventing and/or treating the vulnerable plaque or a disease associated with the vulnerable plaque.

According to the use of the seventh aspect, the vulnerable plaque is one or more selected from the group consisting of rupture-prone plaque, erosion-prone plaque and partially calcified nodular lesions;

preferably, the disease associated with the vulnerable plaque is one or more selected from the group consisting of atherosclerosis, coronary atherosclerotic heart disease (including acute coronary syndrome, asymptomatic myocardial ischemia—latent coronary heart disease, angina pectoris, myocardial infarction, ischemic heart disease, sudden death, and in-stent restenosis), cerebral arteriosclerosis (including stroke), peripheral vascular atherosclerosis (including peripheral arterial occlusive disease, arteriosclerosis of retina, carotid atherosclerosis, renal atherosclerosis, lower extremity atherosclerosis, upper extremity atherosclerosis and atherosclerotic impotence), aortic dissection, hemangioma, thromboembolism, heart failure, and cardiogenic shock.

The eighth aspect of the present invention provides a method for preventing and/or treating a disease associated with the presence of CD44 molecule activation, the method comprises: the nanocarrier delivery system according to the first aspect or the second aspect, the drug according to the forth aspect, or the diagnostic preparation according to the fifth aspect are administered to a subject in need thereof.

The ninth aspect of the present invention provides a method for preventing and/or treating the vulnerable plaque or a disease associated with the vulnerable plaque, the method comprises: the nanocarrier delivery system according to the first aspect or the second aspect, the drug according to the forth aspect, or the diagnostic preparation according to the fifth aspect are administered to a subject in need thereof;

preferably, the vulnerable plaque is one or more selected from the group consisting of rupture-prone plaque, erosion-prone and partially calcified nodular lesions;

more preferably, the disease associated with the vulnerable plaque is one or more selected from the group consisting of atherosclerosis, coronary atherosclerotic heart disease (including acute coronary syndrome, asymptomatic myocardial ischemia—latent coronary heart disease, angina pectoris, myocardial infarction, ischemic heart disease, sudden death, and in-stent restenosis), cerebral arteriosclerosis (including stroke), peripheral vascular atherosclerosis (including peripheral arterial occlusive disease, arteriosclerosis of retina, carotid atherosclerosis, renal atherosclerosis, lower extremity atherosclerosis, upper extremity atherosclerosis and atherosclerotic impotence), aortic dissection, hemangioma, thromboembolism, heart failure, and cardiogenic shock.

The tenth aspect of the present invention provides a method for diagnosing a disease associated with the presence of CD44 molecule activation, characterized in that, the method comprises: the nanocarrier delivery system according to the first aspect or the second aspect, the drug according to the forth aspect, or the diagnostic preparation according to the fifth aspect are administered to a subject in need thereof.

To sum up, the nanocarrier delivery system of the present invention has the following advantages for diseases with the presence of CD44 molecule activation:

1) The nanocarrier delivery system of the present invention can specifically bind to activated CD44 molecules and can realize stable and sustained release of drugs.

2) CD44 on the cell surface in vulnerable plaque is induced and activated by extracellular matrix microenvironment, and a large amount of CD44 is overexpressed, and the affinity of CD44-HA is significantly improved, so that the interaction between CD44 and HA in vulnerable plaque has extremely significant affinity specificity. Therefore, CD44 in vulnerable plaque becomes an excellent target of the nanocarrier delivery system for targeting vulnerable plaque.

3) The nancarrier delivery system for targeting vulnerable plaque can actively target into vulnerable plaque and combine with focus cells. Therefore, the delivery system can realize the sustained release of the loaded substance at the focus, significantly increase and continuously maintain the concentration of the substance in the focus area, thereby improving the diagnosis or treatment effect of the delivery system.

4) The nanocarrier delivery system targeting vulnerable plaque according to the present invention may also be loaded with CD44 activating substances, i.e., CD44 activating agents such as IL5, IL12, IL18, TNF-$\alpha$, LPS. Loading CD44 activator can promote the further activation of CD44 on the surface of focus cells, and can enlarge the targeted affinity of CD44 to hyaluronic acid in a short time, and can significantly increase the concentration of targeted nanocarrier composition bound to the cell surface, which has positive significance for tracer diagnosis and treatment of vulnerable plaque, because it can significantly increase the concentration of tracer or therapeutic agent compound in a short time to improve diagnostic resolution or treatment effect.

BRIEF DESCRIPTION OF THE DRAWINGS

To fully understand the content of the present invention, the present invention is further described in detail below by referring to the specific examples and the accompanying drawings, wherein.

In order to further understand the present invention, the specific embodiments of the present invention are described in detail below with reference to the Examples. It is to be understood, however, that the descriptions are only intended to further illustrate the features and advantages of the present invention and are not intended to limit the claims of the present invention in any way.

DETAILED DESCRIPTION OF EMBODIMENTS

The present invention will be further described below by specific examples, but it should be understood that these examples are only for the purpose of more detailed description and should not be construed as limiting the present invention in any form.

The section gives a general description of the materials and experimental methods used in the test of the present invention. Although many materials and operation methods to achieve the purpose of the present invention are well known in the art, the present invention is still described herein as much detail as possible. It is clear to a person skilled in the art that the materials and operation methods in the present invention are well known in the art in the context, unless otherwise specified.

EXAMPLE 1

Preparation of Liposome Nano Vesicles
(LP1-(R)-HA) which are Loaded with Rosuvastatin
(R) and Modified by Hyaluronic Acid (HA)

In this example, liposome nano vesicles LP1-(R)-HA, which are loaded with a therapeutic agent, are prepared by the thin-film dispersion method. The surfaces of the nano vesicles of the above liposome delivery systems are partially modified by the targeting ligand hyaluronic acid (abbreviated as "HA") and are loaded with rosuvastatin (represented by the abbreviation "R") which is a substance for preventing and/or treating the vulnerable plaque or a disease associated with the vulnerable plaque.

(1) Preparation of LP1-(R) Liposome Nano Vesicle
Suspension 4 mg of distearoyl phosphatidylcholine (DSPC), cholesterol, dimyristoyl phosphoethanolamine (DMPE) (mole ratio is 4:1:1) were weighed and added drug rosuvastatin (R) (the mole ratio of total drug to lipid is 1:10), and then dissolved with 10 mL of chloroform. The organic solvent was removed by means of slow rotary evaporation (65° C. water bath, 90 r/min, 30 min) to form a thin-film on the wall of the container. The container was placed in a constant-temperature water bath kettle at 50° C. to fully hydrate the thin-film for 30 min, so as to form a crude liposome nano vesicle suspension. The crude liposome nano vesicle suspension was ultrasonicated in an ultrasound bath, then the suspension was further ultrasonicated for 3 min (amplitude 20, interval 3 s) with a probe-type ultrasonicator. The unencapsulated drugs in the refined liposome nano vesicle suspension was removed by sephadex column G-100.

(2) Activation and Coupling of Hyaluronic Acid
("HA")

Figure 1:
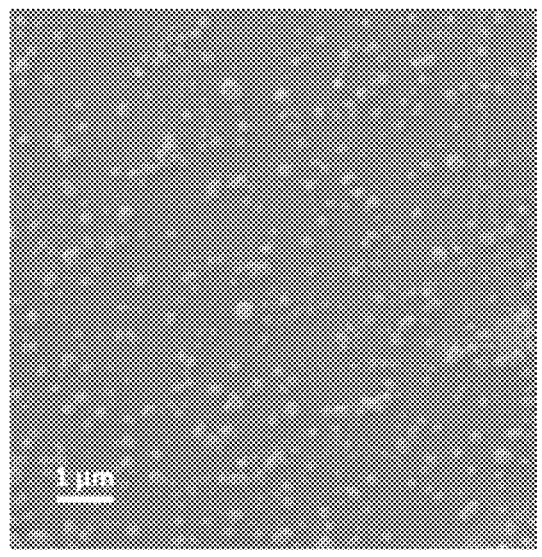
FIG. 1 is the electron micrograph of LP1-(R)-HA in Example 1.
Figure 2:
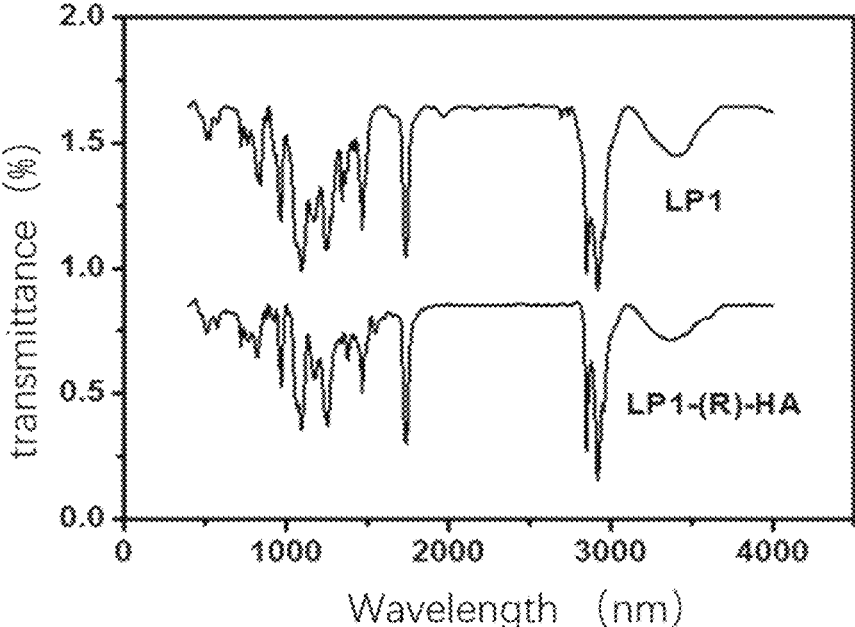
FIG. 2 is the infra-red spectrogram of LP1-(R)-HA in Example 1.

1 g of HA (having a molecular weight of about 100 KDa) was completely dissolved in ultrapure water, and 0.1 g of 1-(3-dimethylaminopropyl)-3-ethylcarbodiimide hydrochloride (EDC.HCl) and 0.12 g of N-hydroxysulfosuccinimide (sulfo-NHS) coupling agent were added to activate the carboxyl group. After the solution was stirred at room temperature for 1 hour, anhydrous ethanol was added to precipitate the activated HA. The precipitation was filtered, washed with ethanol and dried in vacuo to give the activated HA. The same was formulated to a 0.1 mg mL-1 aqueous solution, and 0.2 mL of the solution was transferred and dissolved in the liposome nano vesicle suspension obtained in the above step (1), for coupling the activated carboxyl group in the activated HA to the amino group of the DSPE molecule incorporated in the lipid bilayer of the liposome nano vesicle via forming amide bonds, to obtain three liposome delivery system LP1-(R)-HA, which were loaded with a therapeutic agent. FIG. 1 is the electron micrograph of LP1-(R)-HA. FIG. 2 is the infra-red spectrogram of LP1-(R)-HA.

EXAMPLE 2

Preparation of Liposome Nano Vesicles
(LP1-(R)-SP) which are Loaded with Rosuvastatin
(R) and Modified by Selectin (SP)

In this example, liposome nano vesicles LP1-(R)-SP, which are loaded with a therapeutic agent, are prepared by the thin-film dispersion method. The surfaces of the nano vesicles of the above liposome delivery systems are partially modified by the targeting ligand selectin (abbreviated as "SP") and are loaded with rosuvastatin (represented by the abbreviation "R") which is a substance for preventing and/or treating the vulnerable plaque or a disease associated with the vulnerable plaque.

(1) Preparation of LP1-(R) Liposome Nano Vesicles

Preparation of LP1-(R) liposome nano vesicles according to the method of Example 1.

(2) Activation and Coupling of Selectin (SP)

Figure 3:
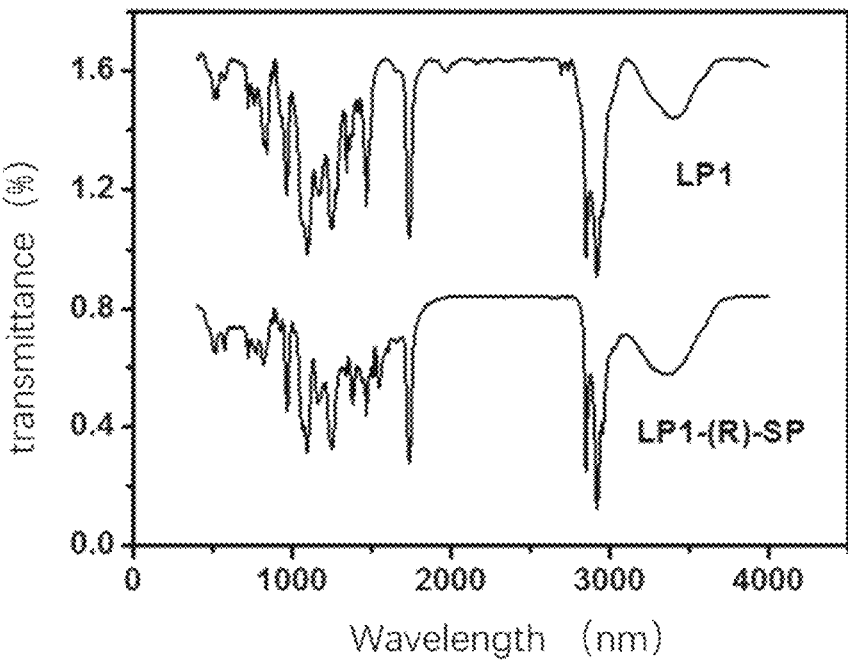
FIG. 3 is the characterization diagram of LP1-(R)-SP in Example 2.

1 mg of SP was completely dissolved in ultrapure water, and 0.5 mg of 1-(3-dimethylaminopropyl)-3-ethylcarbo-diimide hydrochloride (EDC.HCl) and 0.5 mg of N-hydrox-ysulfosuccinimide (sulfo-NHS) coupling agent were added to activate the carboxyl group. After the solution was stirred at room temperature for 1 hour, purified the activated selectin by ultrafiltration, and dissolved in the liposome nano vesicle suspension obtained in the above step (1), for coupling the activated carboxyl group in the activated SP to the amino group of the DMPE molecule incorporated in the lipid bilayer of the liposome nano vesicle via forming amide bonds, to obtain three liposome delivery system LP1-(R)-SP, which were loaded with a therapeutic agent. FIG. 3 is the characterization diagram of LP1-(R)-SP.

EXAMPLE 3

Preparation of Liposome Nano Vesicles (LP1-(R)-HA/Tat) which are Loaded with Rosuvastatin (R) and Modified by Hyaluronic Acid (HA) and Membrane Penetrating Peptide (Tat) Simultaneously In this example, liposome nano vesicles LP1-(R)-HA/Tat, which are loaded with a therapeutic agent, are prepared by the thin-film dispersion method. The surfaces of the nano vesicles of the above liposome delivery systems are partially modified by the targeting ligand hyaluronic acid (abbreviated as "HA") and membrane penetrating peptide (Tat) and are loaded with rosuvastatin (represented by the abbreviation "R") which is a substance for preventing and/or treating the vulnerable plaque or a disease associated with the vulnerable plaque.

3.1 Preparation of LP1-(R) Liposome Nano Vesicles

Preparation of LP1-(R) liposome nano vesicles according to the method of Example 1.

3.2 Activation and Coupling of Hyaluronic Acid ("HA")

10 mg of HA (having a molecular weight of about 10 KDa) was completely dissolved in ultrapure water, and 5 mg of 1-(3-dimethylaminopropyl)-3-ethylcarbodiimide hydrochloride (EDC.HCl) and 5 mg of N-hydroxysulfosuccinim-ide (sulfo-NHS) coupling agent were added to activate the carboxyl group. After the solution was stirred at room temperature for 1 hour, anhydrous ethanol was added to precipitate the activated HA. The precipitation was filtered, washed with ethanol and dried in vacuo to give the activated HA. The same was formulated to a 0.1 mg mL-1 aqueous solution.

1 mg of Tat was completely dissolved in PBS buffer, and 0.1 g of 1-(3-dimethylaminopropyl)-3-ethylcarbodiimide hydrochloride (EDC.HCl) and 0.12 g of N-hydroxysulfos-uccinimide (sulfo-NHS) coupling agent were added to acti-vate the carboxyl group. After the solution was stirred at room temperature for 1 hour, purified remove unreacted small organic molecules by ultrafiltration. The activated Tat was formulated to a 0.1 mg mL-1 aqueous solution.

Figure 4:
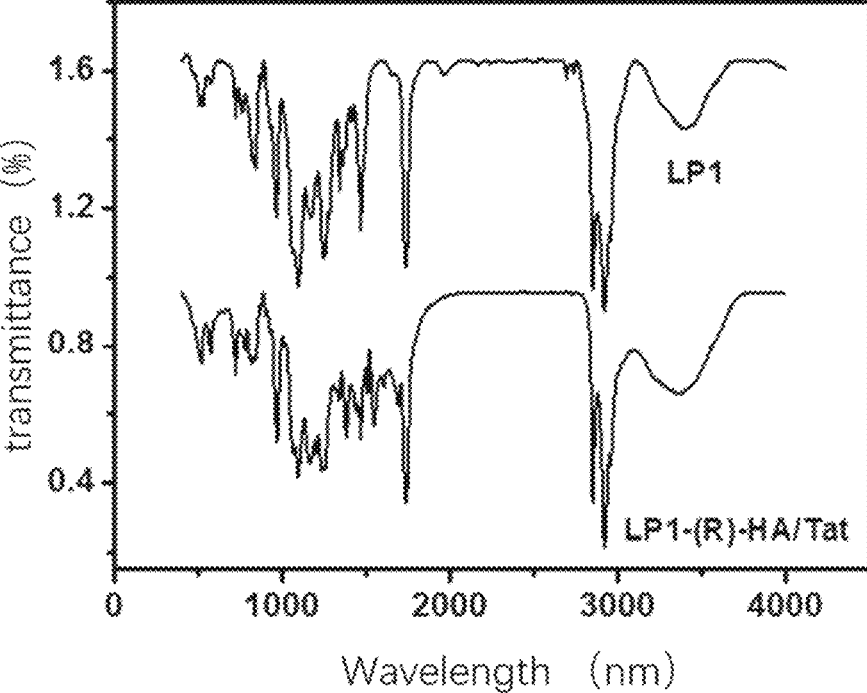
FIG. 4 is the characterization diagram of LP1-(R)-HA/Tat in Example 3.

1 mL of the HA solution and 0.5 mL Tat solution was transferred and dissolved in the purified LP1-(R) liposome nano vesicle solution, for coupling the activated carboxyl group in the activated HA and Tat to the amino group of the DMPE molecule incorporated in the lipid bilayer of the liposome nano vesicle via forming amide bonds, to realize double coupling of HA and Tat on LP1-(R), and obtain target recognition nano carrier LP1-(R)-HA/Tat. FIG. 4 is the infra-red characterization diagram of LP1-(R)-HA/Tat.

EXAMPLE 4

Preparation of Liposome Nano Disks (LP2-(At)-HA) which are Loaded with Atorvastatin (At) and Modified by Hyaluronic Acid (HA) and PEG Simultaneously

(1) Preparation of Liposome Nano Disks LP2-(At) which are Loaded with Atorvastatin (At)

4 mg of 1,2-dimyristoyl-sn-glycero-3-phosphocholine (DMPC), 1,2-di-n-heptadecanoyl phosphatidylcholine (DHPC) with short chain, dimyristoyl phosphoethanolamine (DMPE) (mole ratio is 7:2:1) were weighed and added drug atorvastatin (At) (the mole ratio of total drug to lipid is 1:10), and then dissolved with 10 mL of chloroform. The organic solvent was removed by means of slow rotary evaporation (65° C. water bath, 90 r/min, 30 min) to form a thin-film on the wall of the container. 10 mL water (the concentration is 1.0 mg/mL) was added into the round bottom flask, and the flask was placed in a constant-temperature water bath kettle at 50° C. to fully hydrate the thin-film, so as to form a crude liposome nano disk suspension. The crude liposome nano disk suspension was ultrasonicated in an ultrasound bath, then the suspension was further ultrasonicated for 3 min (amplitude 20, interval 3 s) with a probe-type ultrasonicator. The unencapsulated drugs in the refined liposome nano disk suspension was removed by sephadex column G-100.

(2) Activation and Coupling of Hyaluronic Acid ("HA")

Figure 5:
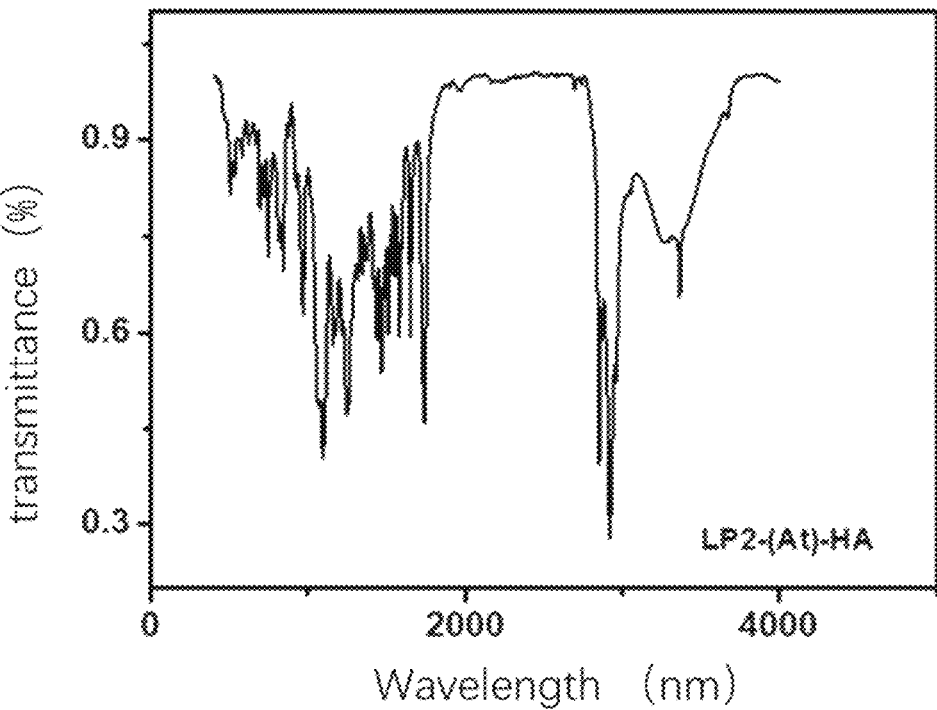
FIG. 5 is the characterization diagram of LP2-(At)-HA in Example 4.

1 g of HA (having a molecular weight of about 100 KDa) was completely dissolved in ultrapure water, and 0.1 g of 1-(3-dimethylaminopropyl)-3-ethylcarbodiimide hydro-chloride (EDC.HCl) and 0.12 g of N-hydroxysulfosuccin-imide (sulfo-NHS) coupling agent were added to activate the carboxyl group. After the solution was stirred at room temperature for 1 hour, anhydrous ethanol was added to precipitate the activated HA. The precipitation was filtered, washed with ethanol and dried in vacuo to give the activated HA. The same was formulated to a 0.1 mg mL-1 aqueous solution, and 0.2 mL of the solution was transferred and dissolved in the liposome nano disk suspension obtained in the above step (1), for coupling the activated carboxyl group in the activated HA, the amino group of PEG-NH2 (molecu-lar weight 1000) and the amino group of the DMPE mol-ecule incorporated in the lipid bilayer of the liposome nano disk via forming amide bonds, to obtain three liposome delivery system LP2-(At)-HA, which were loaded with a therapeutic agent. FIG. 5 is the characterization diagram of LP2-(At)-HA. If PEG does not need to be modified, the above step of adding PEG-NH2 can be omitted to obtain LP2-(At)-HA without PEG modification.

EXAMPLE 5

Preparation of Liposome Nano Disks (LP2-(At)-SEP/IM7) which are Loaded with Atorvastatin (At) and Modified by Self Peptide (SEP) and Monoclonal Antibody IM7

(1) Preparation of Liposome Nano Disks which are Loaded with Atorvastatin (At)

Preparation of liposome nano disks according to the method of Example 4.

(2) Activation and Coupling of SEP or IM7

1 mg of SEP was completely dissolved in ultrapure water, and 0.5 mg of 1-(3-dimethylaminopropyl)-3-ethylcarbo-diimide hydrochloride (EDC.HCl) and 0.5 mg of N-hydrox-ysulfosuccinimide (sulfo-NHS) coupling agent were added to activate the carboxyl group. After the solution was stirred at room temperature for 1 hour, purified the activated SEP by ultrafiltration and centrifugation. 1 mg of IM7 was completely dissolved in ultrapure water, and 0.1 mg of 1-(3-dimethylaminopropyl)-3-ethylcarbodiimide hydrochloride (EDC.HCl) and 0.1 mg of N-hydroxysulfosuccinimide (sulfo-NHS) coupling agent were added to activate the carboxyl group, purified the activated IM7 by ultrafiltration and centrifugation.

Figure 6:
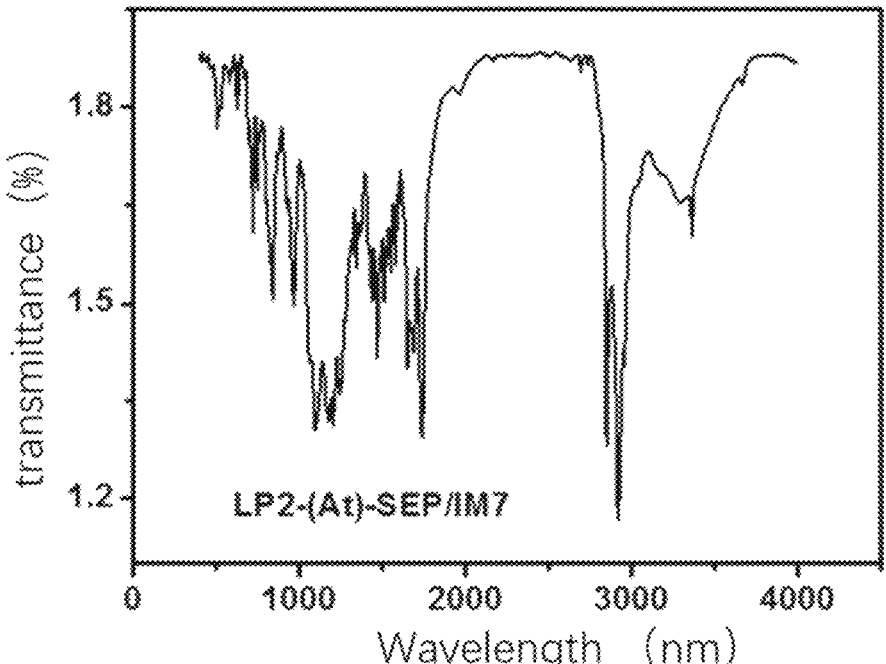
FIG. 6 is the characterization diagram of LP2-(At)-SEP/IM7 in Example 5.

Dissolved the activated SEP or IM7 in the purified LP2-(At) solution, to realize double coupling of SEP/IM7 on LP2-(At), obtained target recognition nano disk LP2-(At)-SEP/IM7. FIG. 6 is the characterization diagram of LP2-(At)-SEP/IM7. If SEP does not need to be modified, the above step of activating and coupling SEP can be omitted to obtain LP2-(At)-IM7 without SEP modification.

EXAMPLE 6

Preparation of Liposome Nano Disks (LP2-(At/miRNA-33a)-IM7) which are Loaded with Atorvastatin (At) and Micro RNA (miRNA-33a) and Modified by Monoclonal Antibody IM7

(1) Preparation of Liposome Nano Disks LP2-(At) which are Loaded with Atorvastatin (At) and Micro RNA (miRNA-33a)

4 mg of DOTAP, 1,2-di-n-heptadecanoyl phosphatidyl-choline (DHPC) with short chain, dimyristoyl phosphoetha-nolamine (DMPE) were weighed with mole ratio of 7:2:1 and added drug atorvastatin (At) (the mole ratio of total drug to lipid is 1:10), and then dissolved with 10 mL of chloro-form. The organic solvent was removed by means of slow rotary evaporation (65° C. water bath, 90 r/min, 30 min) to form a thin-film on the wall of the container. 10 mL water (the concentration is 1.0 mg/mL) was added into the round bottom flask, and the flask was placed in a constant-tem-perature water bath kettle at 50° C. to fully hydrate the thin-film, so as to form a crude liposome nano disk suspen-sion. The crude liposome nano disk suspension was ultra-sonicated in an ultrasound bath, then the suspension was further ultrasonicated for 3 min (amplitude 20, interval 3 s) with a probe-type ultrasonicator to obtain refined liposome nano disk suspension. The unencapsulated atorvastatin in the refined liposome nano disk suspension was removed by sephadex column G-100. After the filtrate is concentrated, a certain amount of microRNA (miRNA-33a) was added and incubated for 2 hours to promote the binding of the microRNA on the surface of the nano disk. The product is stored at a low temperature of 4□ for later use.

Figure 7:
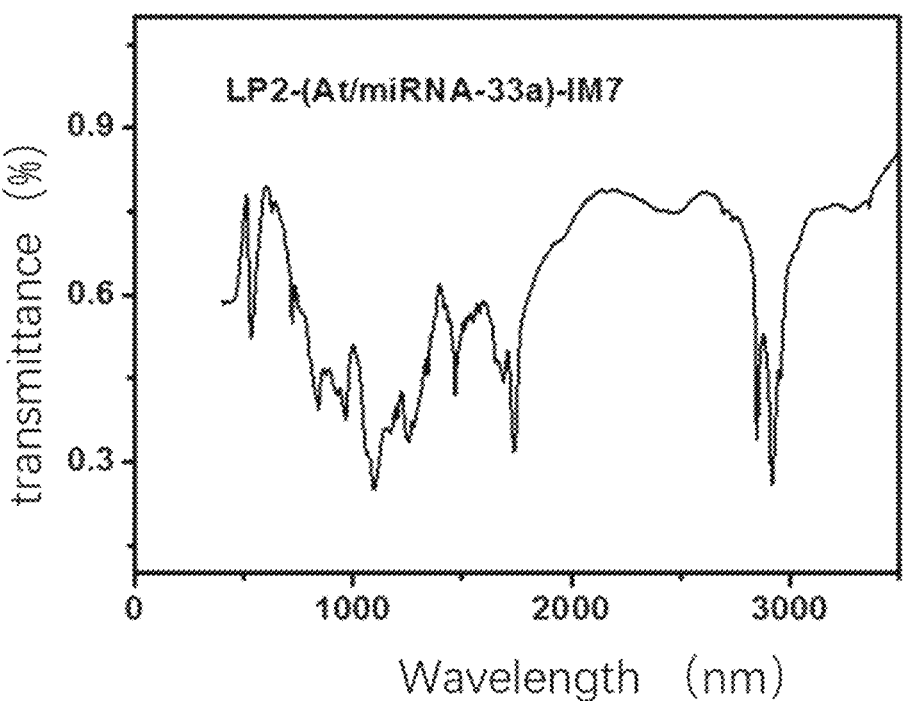
FIG. 7 is the characterization diagram of LP2-(At/miRNA-33a)-IM7 in Example 6.

1 mg of IM7 was completely dissolved in ultrapure water, and 0.5 mg of 1-(3-dimethylaminopropyl)-3-ethylcarbo-diimide hydrochloride (EDC.HCl) and 0.5 mg of N-hydrox-ysulfosuccinimide (sulfo-NHS) coupling agent were added to activate the carboxyl group, purified the activated sulfo-NHS-IM7 by ultrafiltration and centrifugation. Dissolved the activated it in the purified LP2-(At/miRNA-33a) solu-tion, to realize double coupling of IM7 on LP2-(At/miRNA-33a), obtain target recognition nano disk LP2-(At/miRNA-33a)-IM7. FIG. 7 is the infra-red characterization diagram of LP2-(At/miRNA-33a)-IM7.

EXAMPLE 7

Preparation of Liposome Nano Disks (LP2-(AuNP/R)-OPN) which are Loaded with Rosuvastatin (R)/ Gold Nanoparticles (AuNP) and Modified by Osteopontin (OPN)

7.1 Preparation of Gold Nanoparticles (AuNP)

100 mL 1 mM HAuCl4 solution was prepared and heated to boil, added 1 mL of newly prepared 0.1M sodium borohydride under vigorous stirring to obtain AuNPs, puri-fied the solution by ultrafiltration, and concentrated the solution to obtain 1 mM AuNPs.

7.2 Preparation of Liposome Nano Disks LP2-(AuNP/R) which are Loaded with Rosuvastatin (R) and Gold Nanoparticles (AuNP)

4 mg of 1,2-dimyristoyl-sn-glycero-3-phosphocholine (DMPC), 1,2-di-n-heptadecanoyl phosphatidylcholine (DHPC) with short chain, dimyristoyl phosphoethanolamine (DMPE) were weighed with mole ratio of 7:2:1 and added drug rosuvastatin (R) (the mole ratio of total drug to lipid is 1:10), and then dissolved with 10 mL of chloroform. The organic solvent was removed by means of slow rotary evaporation (65° C. water bath, 90 r/min, 30 min) to form a thin-film on the wall of the container. The flask was placed in a constant-temperature water bath kettle at 50° C. to fully hydrate the thin-film for 30 min, added 1 mL purified AuNPs (1 mM) solution. The crude liposome nano disk suspension was ultrasonicated in an ultrasound bath, then the suspen-sion was further ultrasonicated for 3 min (amplitude 20, interval 3 s) with a probe-type ultrasonicator. The unencap-sulated rosuvastatin and AuNPs in the refined liposome nano disk suspension was removed by sephadex column G-100.

7.3 Preparation of Liposome Nano Disks (LP2-(AuNP/R)-OPN) which are Loaded with AuNP/R and Modified by Osteopontin (OPN)

Figure 8:
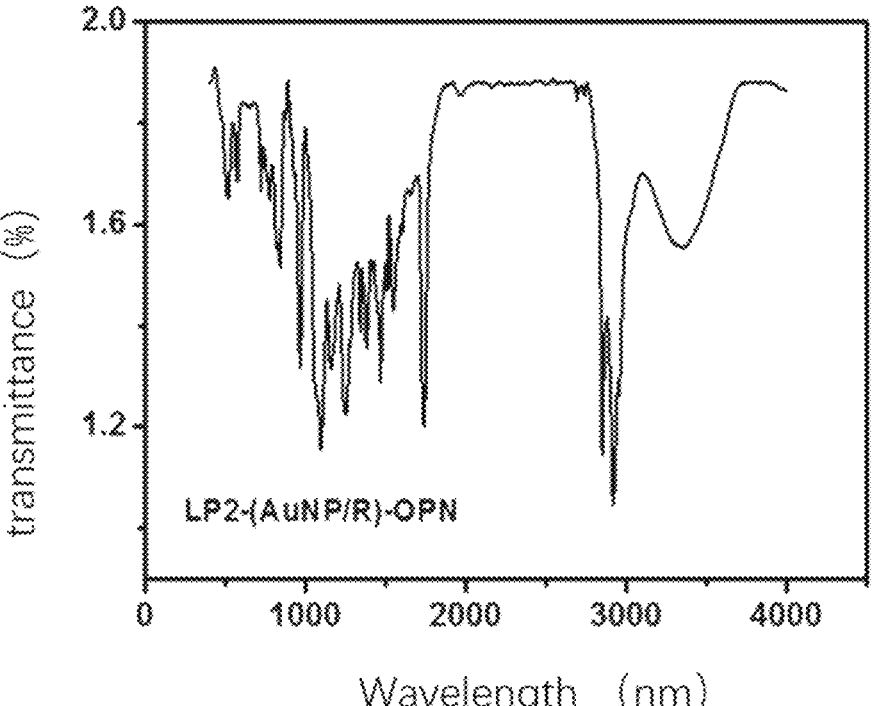
FIG. 8 is the characterization diagram of LP2-(AuNP/R)-OPN in Example 7.

1 mg of OPN was completely dissolved in ultrapure water, and 0.5 mg of 1-(3-dimethylaminopropyl)-3-ethylcarbo-diimide hydrochloride (EDC.HCl) and 0.5 mg of N-hydrox-ysulfosuccinimide (sulfo-NHS) coupling agent were added to activate the carboxyl group. After the solution was stirred at room temperature for 1 hour, purified the activated OPN by ultrafiltration and centrifugation. Dissolved 1.0 mL OPN solution in the purified LP2-(AuNP/R) solution, to realize coupling of OPN on LP2-(AuNP/R). FIG. 8 is the infra-red characterization diagram of LP2-(AuNP/R)-OPN in Example 7.

Replacing raw materials, the inventors also successfully prepared targeted CT tracers LP2-(iopromide)-OPN, LP2-(iodixanol)-OPN and LP2-(iodofluoroalcohol)-OPN by the above similar preparation method.

EXAMPLE 8

Preparation of Liposome Nano Vesicles (LP1-(Fe3O4/DXMS)-HI44a) which are Loaded with Dexamethasone (DXMS) and Magnetic Iron Nanoparticles (Fe3O4 NPs) and Modified by Monoclonal Antibody (HI44a)

8.1 Preparation of Magnetic Iron Nanoparticles (Fe3O4 NPs)

100 mL 10 mM ferric chloride (FeCl3) solution was prepared, added 10 mL of newly prepared 0.1M ammonium hydroxide under vigorous stirring to obtain magnetic iron nanoparticles (Fe3O4 NPs), purified the material by external magnetic field. Concentrated the solution and redispersed it in pure water to prepare 10 mM Fe3O4 NPs.

8.2 Preparation of Liposome Nano Vesicles LP1-(Fe3O4/DXMS) which are Loaded with Dexamethasone (DXMS) and Magnetic Iron Nanoparticles (Fe3O4 NPs)

4 mg of distearoyl phosphatidylcholine (DSPC), cholesterol, dimyristoyl phosphoethanolamine (DMPE) (mole ratio is 4:1:1) were weighed and added drug dexamethasone (DXMS) (the mole ratio of total drug to lipid is 1:10), and then dissolved with 10 mL of chloroform. The organic solvent was removed by means of slow rotary evaporation (65° C. water bath, 90 r/min, 30 min) to form a thin-film on the wall of the container. Added 10 mL purified 1 mM Fe3O4 NPs solution, and the flask was placed in a constant-temperature water bath kettle at 50° C. to fully hydrate the thin-film, so as to form a crude liposome nano vesicle suspension. The crude liposome nano vesicle suspension was ultrasonicated in an ultrasound bath, then the suspension was further ultrasonicated for 3 min (amplitude 20, interval 3 s) with a probe-type ultrasonicator, to obtain a dispersion system formed by fully dispersing liposome vesicles, namely refined liposome vesicle suspension. The unencapsulated drugs and Fe3O4 NPs in the refined liposome nano vesicle suspension was removed by sephadex column G-100.

Figure 9:
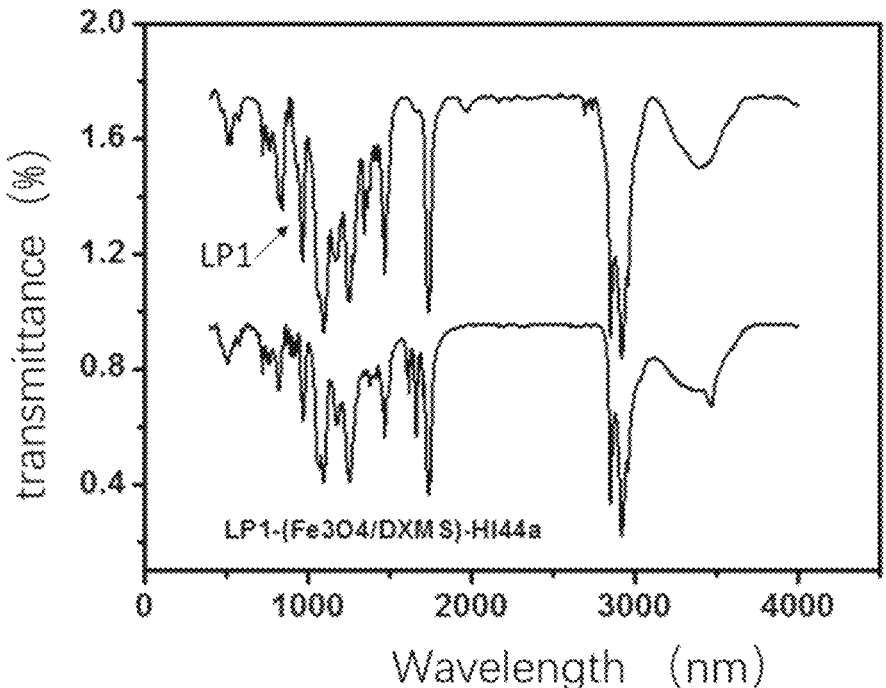
FIG. 9 is the characterization diagram of LP1-(Fe3O4/DXMS)-HI44a in Example 8.

8.3 Preparation of Liposome Nano Vesicles (LP1-(Fe3O4/DXMS)-HI44a) which are Loaded with Fe3O4/DXMS and Modified by HI44a 1 mg of HI44a was completely dissolved in ultrapure water, and 0.5 mg of 1-(3-dimethylaminopropyl)-3-ethylcarbodiimide hydrochloride (EDC.HCl) and 0.5 mg of N-hydroxysulfosuccinimide (sulfo-NHS) coupling agent were added to activate the carboxyl group. After the solution was stirred at room temperature for 1 hour, purified the activated HI44a by ultrafiltration and centrifugation. Dissolved the HI44a solution in the purified LP1-(Fe3O4/DXMS) solution, to realize coupling of HI44a on LP1-(Fe3O4/DXMS), obtain target recognition nano carrier LP1-(Fe3O4/DXMS)-HI44a. FIG. 9 is the characterization diagram of LP1-(Fe3O4/DXMS)-HI44a in Example 8.

Replacing raw materials, the inventors also successfully prepared targeted MRI tracers LP1-(gadoterate meglumine)-

HI44a, LP1-(gadodiamide)-HI44a, LP1-(gadopentetic acid)-HI44a and so on by the above similar preparation method.

EXAMPLE 9

Preparation of Liposome Nano Vesicles (LP1-(Fe3O4/IL-10)-HI44a) which are Loaded with Interleukin 10 (IL-10) and Magnetic Iron Nanoparticles (Fe3O4 NPs) and Modified by Monoclonal Antibody (HI44a)

9.1 Preparation of Magnetic Iron Nanoparticles (Fe3O4 NPs)

Preparation of magnetic iron nanoparticles (Fe3O4 NPs) according to the method of Example 8.

9.2 Preparation of Liposome Nano Vesicles LP1-(Fe3O4/IL-10) which are Loaded with IL-10 and Magnetic Iron Nanoparticles (Fe3O4 NPs)

4 mg of distearoyl phosphatidylcholine (DSPC), cholesterol, dimyristoyl phosphoethanolamine (DMPE) (mole ratio is 4:1:1) were weighed. The organic solvent was removed by means of slow rotary evaporation (65° C. water bath, 90 r/min, 30 min) to form a thin-film on the wall of the container. Added 10 mL purified 1 mM Fe3O4 NPs solution, and the flask was placed in a constant-temperature water bath kettle at 50° C. to fully hydrate the thin-film, so as to form a crude liposome nano vesicle suspension. The crude liposome nano vesicle suspension was ultrasonicated in an ultrasound bath, then the suspension was further ultrasonicated for 3 min (amplitude 20, interval 3 s) with a probe-type ultrasonicator, to obtain a dispersion system formed by fully dispersing liposome vesicles, namely refined liposome vesicle suspension. Concentrated the solution and added 1 mg IL-10 and incubated at room temperature for 10 hours to obtain LP1-(Fe3O4/IL-10). The unencapsulated drugs in the refined liposome nano vesicle suspension was removed by sephadex column G-100.

Figure 10:
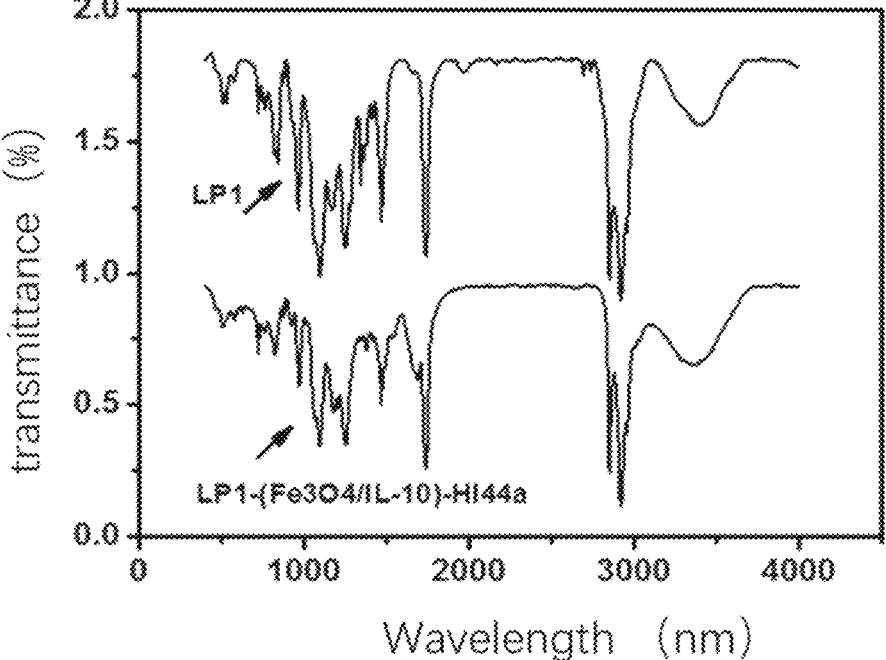
FIG. 10 is the characterization diagram of LP1-(Fe3O4/IL-10)-HI44a in Example 9.

9.3 Preparation of Liposome Nano Vesicles (LP1-(Fe3O4/IL-10)-HI44a) which are Loaded with Fe3O4/IL-10 and Modified by HI44a 1 mg of HI44a was completely dissolved in ultrapure water, and 0.5 mg of 1-(3-dimethylaminopropyl)-3-ethylcarbodiimide hydrochloride (EDC.HCl) and 0.5 mg of N-hydroxysulfosuccinimide (sulfo-NHS) coupling agent were added to activate the carboxyl group. After the solution was stirred at room temperature for 1 hour, purified the activated HI44a by ultrafiltration and centrifugation. Dissolved the HI44a solution in the purified LP1-(Fe3O4/IL-10) solution, to realize coupling of HI44a on LP1-(Fe3O4/IL-10), obtain target recognition nano carrier LP1-(Fe3O4/IL-10)-HI44a. FIG. 10 is the infra-red characterization diagram of LP1-(Fe3O4/IL-10)-HI44a in Example 9.

EXAMPLE 10

Preparation of Liposome Nano Vesicles (LP1-(Asp/Clo)-Col) which are Loaded with Aspirin (Asp) and Clopidogrel (Clo) and Modified by Collagen (Col)

10.1 Preparation of Liposome Nano Vesicles LP1-(Asp/Clo) which are Loaded with Aspirin (Asp) and Clopidogrel (Clo)

4 mg of distearoyl phosphatidylcholine (DSPC), cholesterol, dimyristoyl phosphoethanolamine (DMPE) (mole ratio is 4:1:1) were weighed and added drug aspirin (Asp) and clopidogrel (Clo) (the mole ratio of the drugs is 1:1, and the mole ratio of total drug to lipid is 1:10), and then dissolved with 10 mL of chloroform. The organic solvent was removed by means of slow rotary evaporation (65° C. water bath, 90 r/min, 30 min) to form a thin-film on the wall of the container. The container was placed in a constant-temperature water bath kettle at 50° C. to fully hydrate the thin-film, so as to form a crude liposome nano vesicle suspension. The crude liposome nano vesicle suspension was ultrasonicated in an ultrasound bath, then the suspension was further ultrasonicated for 3 min (amplitude 20, interval 3 s) with a probe-type ultrasonicator. The unencapsulated drugs in the refined liposome nano vesicle suspension was removed by sephadex column G-100.

10.2 Preparation of Loaded Liposome Nano Vesicles (LP1-(Asp/Clo)-Col) which are Modified by Collagen (Col)

Figure 11:
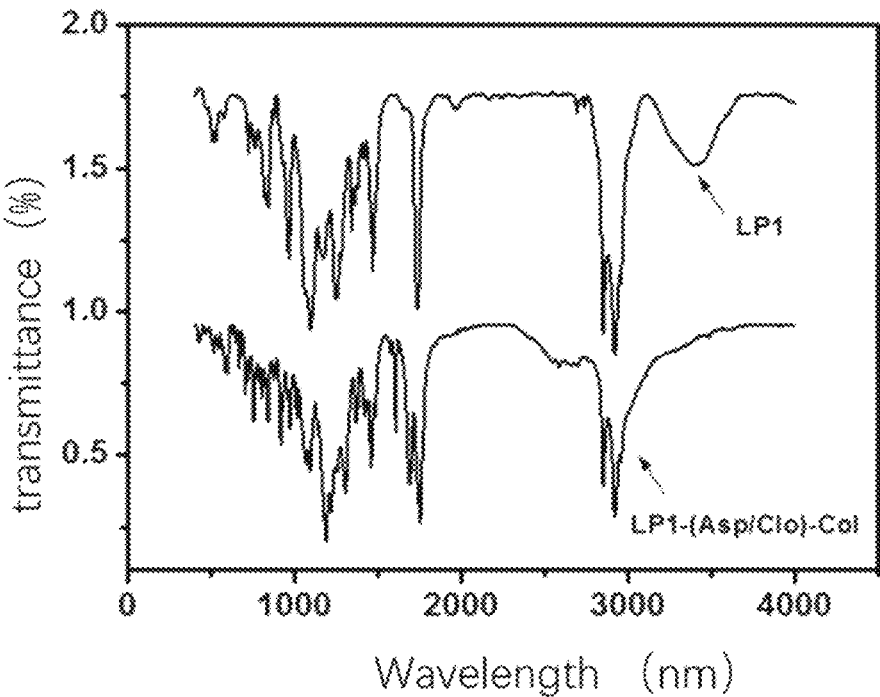
FIG. 11 is the characterization diagram of LP1-(Asp/Clo)-Col in Example 10.

10 mg of Col was completely dissolved in ultrapure water, and 3 mg of 1-(3-dimethylaminopropyl)-3-ethylcarbodiimide hydrochloride (EDC.HCl) and 3 mg of N-hydroxysulfosuccinimide (sulfo-NHS) coupling agent were added to activate the carboxyl group. After the solution was stirred at room temperature for 1 hour, purified the activated Col by ultrafiltration and centrifugation. Dissolved 1.0 mL activated Col in the purified LP1-(Asp/Clo) solution, to realize the coupling of Col on LP1-(Asp/Clo), obtain target recognition liposome vesicles LP1-(Asp/Clo)-Col. FIG. 11 is the infra-red characterization diagram of LP1-(Asp/Clo)-Col in Example 10.

EXAMPLE 11

Preparation of Liposome Nano Vesicles (LP1-(F-FDG)-OPN) which are Loaded with Fluorine 18 (18F)-Labeled Fludeoxyglucose (F-FDG) and Modified by Osteopontin (OPN)

11.1 Preparation of Liposome Nano Vesicles (LP1-(F-FDG)) which are Loaded with F-FDG 4 mg of distearoyl phosphatidylcholine (DSPC), cholesterol, dimyristoyl phosphoethanolamine (DMPE) (mole ratio is 4:1:1) were weighed, and then dissolved with 10 mL of chloroform. The organic solvent was removed by means of slow rotary evaporation (65° C. water bath, 90 r/min, 30 min) to form a thin-film on the wall of the container. Added 10 mL 1 mgmL-1 F-FDG solution (the mole ratio of total drug to lipid is 1:10), and the container was placed in a constant-temperature water bath kettle at 50° C. to fully hydrate the thin-film, so as to form a crude liposome nano vesicle suspension. The crude liposome nano vesicle suspension was ultrasonicated in an ultrasound bath, then the suspension was further ultrasonicated for 3 min (amplitude 20, interval 3 s) with a probe-type ultrasonicator. The unencapsulated drugs in the refined liposome nano vesicle suspension was removed by sephadex column G-100.

11.2 Preparation of Liposome Nano Vesicles (LP1-(F-FDG)) which are Loaded with F-FDG and Modified by Osteopontin (OPN)

Figure 12:
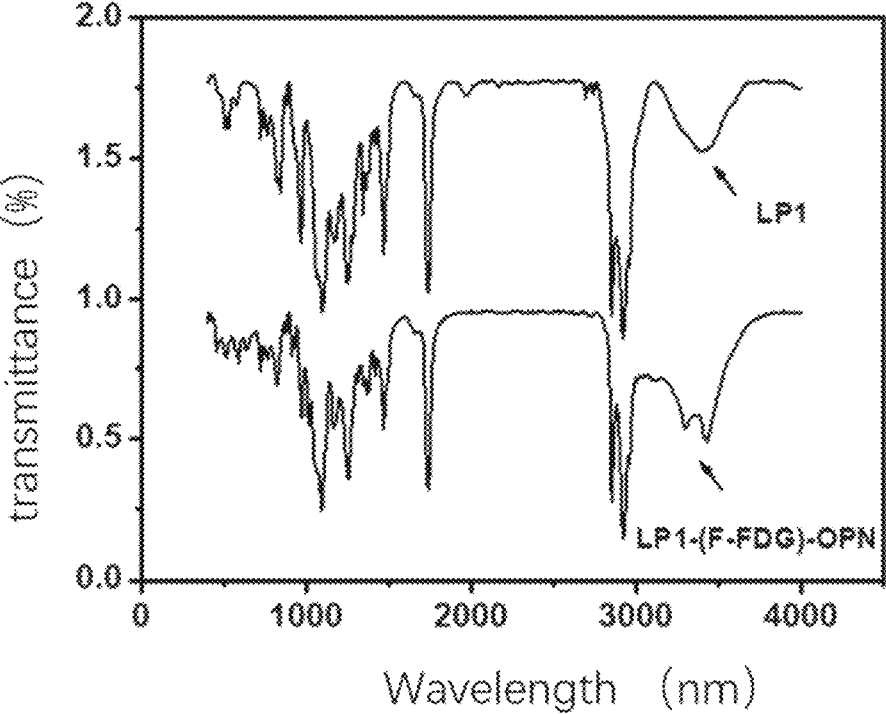
FIG. 12 is the characterization diagram of LP1-(F-FDG)-OPN in Example 11.

1 mg of OPN was completely dissolved in ultrapure water, and 0.5 mg of 1-(3-dimethylaminopropyl)-3-ethylcarbodiimide hydrochloride (EDC.HCl) and 0.5 mg of N-hydroxysulfosuccinimide (sulfo-NHS) coupling agent were added to activate the carboxyl group. After the solution was stirred at room temperature for 1 hour, purified the activated OPN by ultrafiltration and centrifugation. Dissolved the activated OPN in the purified LP1-(F-FDG) solution, to realize coupling of OPN on LP1-(F-FDG), obtain target recognition nano carrier LP1-(F-FDG)-OPN. FIG. 12 is the infra-red characterization diagram of LP1-(F-FDG)-OPN in Example 11.

EXPERIMENTAL EXAMPLE 1

Investigation of Properties of the Nanocarrier Delivery System of the Present Invention In this example, the nanocarrier delivery systems loaded with the therapeutic agent, which are prepared in Example 1, are taken as examples to prove that the carrier delivery system of the present invention has stable and controllable properties and is therefore suitable for the diagnosis, prevention and treatment of the vulnerable plaque or a disease associated with the vulnerable plaque.

1. Method for the Determination of Drug Concentration

The loaded drugs rosuvastatin, atorvastatin, dexamethasone, aspirin, clopidogrel and fluorine 18 (18F)-labeled fludeoxyglucose have strong ultraviolet absorption property, and thus its content can be determined with the HPLC-UV method (using Waters 2487, Waters Corporation, U.S.A.) by using with the ultraviolet absorption property of rosuvastatin, atorvastatin, dexamethasone, aspirin, clopidogrel, fluorine 18 (18F)-labeled fludeoxyglucose. A standard quantitative equation was established with various concentrations of rosuvastatin, atorvastatin, dexamethasone, aspirin, clopidogrel, fluorine 18 (18F)-labeled fludeoxyglucose solution (X) versus the peak area of the HPLC chromatographic peak (Y).

2. Determination of Hydrodynamic Size

The hydrodynamic sizes of the carrier delivery systems LP1-(R)-HA, LP1-(R)-SP, LP1-(R)-HA/Tat, LP2-(At)-HA, LP2-(At)-SEP/IM7, LP2-(At/miRNA-33a)-IM7, LP2-(AuNP/R)-OPN, LP1-(Fe3O4/DXMS)-HI44a, LP1-(Fe3O4/IL-10)-HI44a, LP1-(Asp/Clo)-Col, LP1-(F-FDG)-OPN of the present invention were measured by a laser particle analyzer (BI-Zeta Plus/90 Plus, Brookhaven Instruments Corporation, U.S.A.), and the specific results are shown in Table 1.

3. Determination of Encapsulation Rate

Took a certain quality of drug suspension, added excessive methanol to reflux and extract that load drug, and further adopting ultrasonic extraction to accelerate the drug release from the carrier. The drug content in the resulting liquid was measured by HPLC (Waters 2487, Waters Corporation, U.S.A.), and the encapsulation rate was calculated in accordance with Equation 1.

$$\text{Encapsulation rate } \% = \frac{M_{encapsulated\ drug\ amount}}{M_{added\ drug\ amount}} \times 100\% \qquad \text{Equation 1}$$

4. Determination of Drug-Loading Rate

The method for determining the drug-loading rate is similar to that for determining the encapsulation rate, except that the calculation method is slightly different. Took a certain quality of drug suspension, added excessive methanol to reflux and extract that load drug, and further adopting ultrasonic extraction to accelerate the drug release from the carrier. The drug content in the resulting liquid was measured by HPLC (Waters 2487, Waters Corporation, U.S.A.), and the encapsulation rate was calculated in accordance with the following equation.

$$\text{Drug-loading rate } \% = \frac{M_{encapsulated\ drug\ amount}}{M_{added\ carrier\ amount}} \times 100\% \qquad \text{Equation 2}$$

The drug content in the resulting liquid was measured by HPLC (Waters 2487, Waters Corporation, U.S.A.), and the encapsulation rate was calculated in accordance with Equation 2.

TABLE 1

List of various properties

| Name | Hydrodynamic size (nm) | Drug encapsulation rate (%) | Drug-loading rate (%) | Surface potential (mV) |
|---|---|---|---|---|
| LP1-(R)-HA | 173 | 58.73 ± 1.8 | 2.73 ± 0.24 | −42.3 |
| LP1-(R)-SP | 165 | 59.23 ± 1.6 | 2.23 ± 0.17 | −28.6 |
| LP1-(R)-HA/Tat | 178 | 58.21 ± 1.7 | 2.21 ± 0.12 | −29.1 |
| LP2-(At)-HA | 62 | 68.53 ± 1.2 | 2.53 ± 0.21 | −41.3 |
| LP2-(At)-SEP/IM7 | 68 | 66.42 ± 1.4 | 2.4 ± 0.15 | −28.4 |
| LP2-(At/miRNA-33a)-IM7 | 58 | 68.43 ± 0.85 | 1.8 ± 0.34 | −26.6 |
| LP2-(AuNP/R)-OPN | 72 | 67.53 ± 0.91 | 1.6 ± 0.34 | −28.5 |
| LP1-(Fe$_3$O$_4$/DXMS)-HI44a | 176 | 56.53 ± 1.24 | 2.7 ± 0.34 | −26.8 |
| LP1-(Fe$_3$O$_4$/IL-10)-HI44a | 153 | 41.64 ± 1.13 | 2.1 ± 0.34 | −25.3 |
| LP1-(Asp/Clo)-Col | 165 | 58.83 ± 1.1 | 2.8 ± 0.34 | −24.3 |
| LP1-(F-FDG)-OPN | 158 | 42.53 ± 1.02 | 2.53 ± 0.34 | −23.2 |

Note:
The above data are expressed in the form of "average + standard deviation" of the results of 5 determinations in parallel.

5. Investigation of Long-Term Stability

Figure 13:
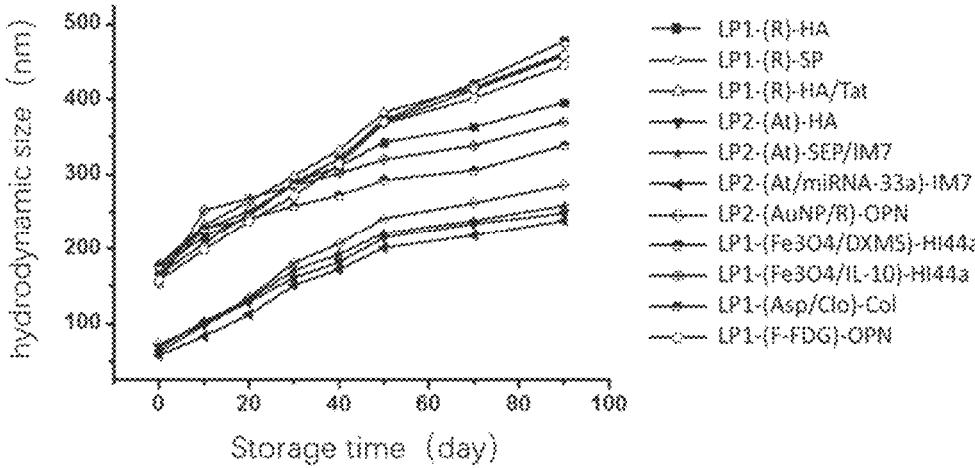
FIG. 13 is the influence of long-term storage on particle size stability in Experimental example 1.

The nanocarrier delivery systems LP1-(R)-HA, LP1-(R)-SP, LP1-(R)-HA/Tat, LP2-(At)-HA, LP2-(At)-SEP/IM7, LP2-(At/miRNA-33a)-IM7, LP2-(AuNP/R)-OPN, LP1-(Fe3O4/DXMS)-HI44a, LP1-(Fe3O4/IL-10)-HI44a, LP1-(Asp/Clo)-Col, LP1-(F-FDG)-OPN of the present invention were stored at 4° C., and sampled at different time points. The changes in the hydrodynamic sizes thereof were detected by a laser particle analyzer (BI-Zeta Plus/90 Plus, Brookhaven Instruments Corporation, U.S.A.), and the results are shown in FIG. 13. FIG. 13 is the influence of long-term storage on particle size stability.

6. Investigation of Long-Term Encapsulation Rate

Figure 14:
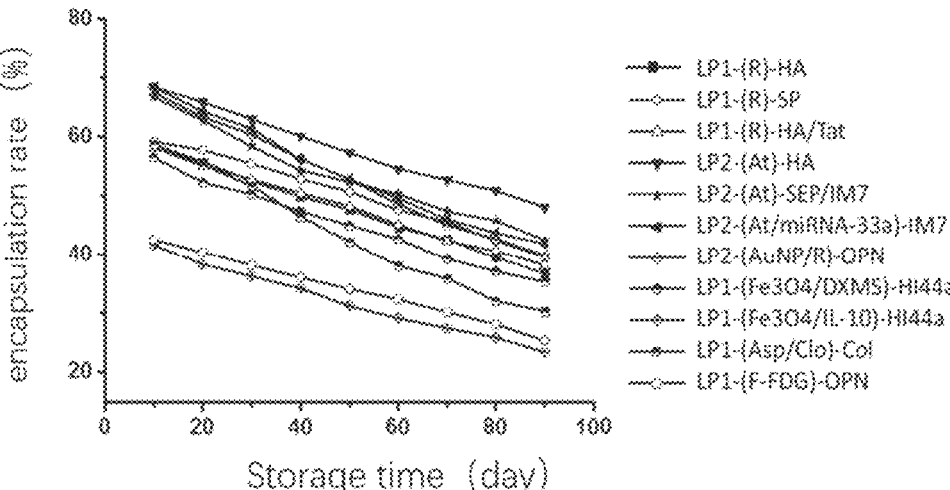
FIG. 14 is the influence of long-term storage on encapsulation rate in Experimental example 1.

The nanocarrier delivery systems LP1-(R)-HA, LP1-(R)-SP, LP1-(R)-HA/Tat, LP2-(At)-HA, LP2-(At)-SEP/IM7, LP2-(At/miRNA-33a)-IM7, LP2-(AuNP/R)-OPN, LP1-(Fe3O4/DXMS)-HI44a, LP1-(Fe3O4/IL-10)-HI44a, LP1-(Asp/Clo)-Col, LP1-(F-FDG)-OPN of the present invention were stored at 4° C., and sampled at different time points, and the free drug was removed by ultrafiltration and centrifugation to detect changes in the encapsulation rate thereof, and the results are shown in FIG. 14. FIG. 14 is the influence of long-term storage on encapsulation rate.

7. Study on In Vitro Drug Release Performance 2 mL of the nanocarrier delivery systems LP1-(R)-HA, LP1-(R)-SP, LP1-(R)-HA/Tat, LP2-(At)-HA, LP2-(At)-SEP/IM7, LP2-(At/miRNA-33a)-IM7, LP2-(AuNP/R)-OPN, LP1-(Fe3O4/DXMS)-HI44a, LP1-(Fe3O4/IL-10)-HI44a, LP1-(Asp/Clo)-Col, LP1-(F-FDG)-OPN of the present invention were placed in a dialysis bag and sealed. The dialysis bag was then placed in 50 mL of release medium (PBS solution, pH=7.4) and incubated at 37° C. for 120 h. 2 mL of the release liquid was taken at different time points and the same volume of PBS solution was replenished. The drug content in the release liquid was detected by HPLC (Waters 2487, Waters Corporation, U.S.A.), and the cumulative drug release rate was calculated according to Equation 3.

$$CRP\% = \frac{V_e \sum_{1}^{n-1} C_i + V_0 C_n}{M_{drug}} \times 100\% \qquad \text{Equation 3}$$

The meaning of each parameter in Equation 3 is as follows:

CRP: cumulative drug release rate

Ve: displacement volume of the release liquid, Ve being 2 mL herein

V0: volume of the release liquid in the release system, V0 being 50 mL herein

Ci: concentration of drug in the release liquid at the ith replacement and sampling, in μg/mL M Drug: total mass of drug in the cerasome or liposome delivery system, in μg n: number of times for replacement of the release liquid Cn: drug concentration in the release system measured after the nth replacement of the release liquid.

Figure 15:
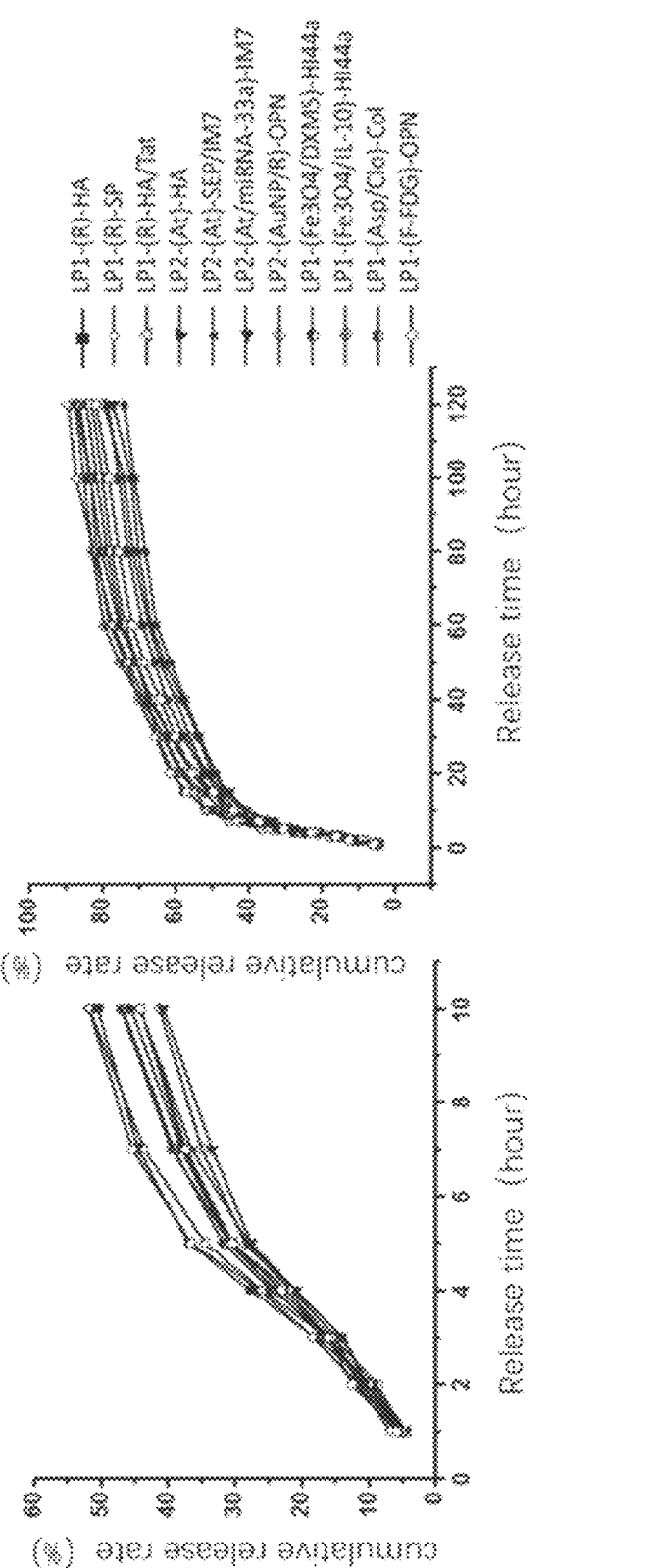
FIG. 15 is the in vitro cumulative drug release rate of the liposome carrier in Experimental example 1.

In vitro release is an important index for evaluating the nanoparticle delivery systems. FIG. 15 is a graph showing the change in cumulative drug release rate of the liposome delivery system of the present invention.

EXPERIMENTAL EXAMPLE 2

Study on Targeting Mechanism

In this example, the density of CD44 on the surface of endothelial cells at vulnerable plaques and its affinity for HA are studied, thus providing an experimental basis for selecting CD44 within the vulnerable plaque as a target for the delivery system of the present invention for targeting the vulnerable plaque.

1) Comparison of CD44 Content on the Surface of Endothelial Cells at Arterial Vulnerable Plaques and on the Surface of Endothelial Cells of Normal Arterial Vessel Walls of Mice Construct a mouse model of atherosclerotic vulnerable plaque.

Figure 16:
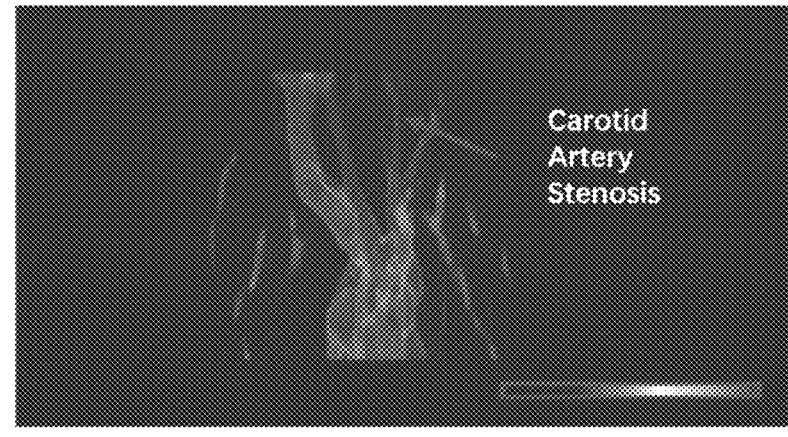
FIG. 16 is the image of the nuclear magnetic resonance imaging of a mouse atherosclerotic vulnerable plaque model constructed in Experimental example 2.
Figure 16:
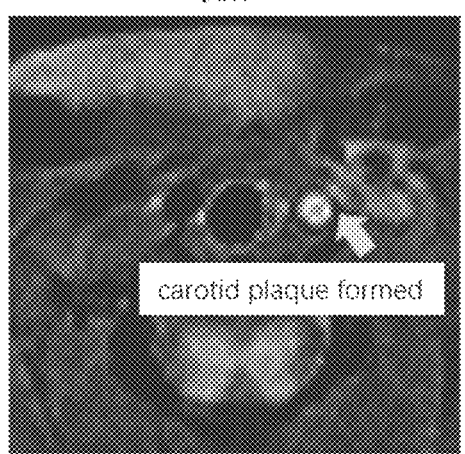

SPF-grade ApoE−/− mice (10 weeks old, weight 20±1 g) are taken as experimental animals. The mice were fed with an adaptive high-fat diet (fat 10% (w/w), cholesterol 2% (w/w), sodium cholate 0.5% (w/w), and the rest being normal feed for mice) for 4 weeks, and then anaesthetized by intraperitoneal injection of 1% sodium pentobarbital (prepared by adding 1 mg of sodium pentobarbital to 100 ml of normal saline) at a dose of 40 mg/kg. Then, the mice were fixed on the surgical plate in the supine position, disinfected around the neck with 75% (v/v) alcohol, the neck skin was cut longitudinally, the anterior cervical gland was bluntly separated, and the beating left common carotid artery can be observed on the left side of the trachea. The common carotid artery was carefully separate to the bifurcation. A silicone cannula with a length of 2.5 mm and an inner size of 0.3 mm was placed on the outer periphery of the left common carotid artery. The proximal and distal segments of the cannula were narrowed and fixed by filaments. Local tightening causes rapid blood flow in the proximal end with increased shear force, and thus damage to the intima of the blood vessel. The carotid artery was repositioned and the neck skin was intermittently sutured. All operations were performed under a 10× stereomicroscope. After awakened from the surgery, the mice were returned to the cage, where the ambient temperature was maintained at 20~25° C., and the light was kept under a 12 h/12 h light/dark cycle. At the 4th week after the surgery, lipopolysaccharide (LPS) (1 mg/kg in 0.2 ml phosphate buffered saline, Sigma, U.S.A.) was injected intraperitoneally twice a week for 10 weeks to induce chronic inflammation. At the 8th week after the surgery, mice were placed in a 50 ml syringe (sufficient vents reserved) to trigger restrictive mental stress, 6 hours/day, 5 days per week for a total of 6 weeks. The mouse model of atherosclerotic vulnerable plaque was completed at the 14th week after the surgery. FIGS. 16(a) and (b) show images of the nuclear magnetic resonance imaging of the mouse atherosclerotic vulnerable plaque model. It can be seen from the part at which the arrow points that the left carotid plaque has been formed, suggesting successful modeling, and the right carotid can be used as a normal arterial vessel wall for comparison.

The endothelial cells of normal arterial vessels and endothelial cells at arterial vulnerable plaques of model mice are taken for CD44 content determination by immunohisto chemical staining and image analysis, and the specific experimental method is as follow:

The mouse carotid atherosclerotic vulnerable plaque specimens were taken and fixed with 10 mL/L formaldehyde aqueous solution, embedded with paraffin, sectioned in 4

μm, dewaxed in a conventional manner, hydrated, and CD44 content was detected by streptavidin-biotin-peroxidase complex method (SABC). The specimen was immersed in 30 mL/L H2O2 aqueous solution to block the activity of endogenous peroxidase, and the specimen was placed in a citrate buffer for antigen microwave repair. Then 50 g/L bovine serum albumin (BSA) blocking solution was added dropwise and the sample was allowed to stand at room temperature for 20 min. Then, a murine anti-CD44 polyclonal antibody (1:100) was added dropwise, the sample was placed in a refrigerator at 4° C. overnight, and incubated at 37° C. for 1 h. The specimen was washed, then the biotinylated goat anti-mouse IgG was added dropwise and reacted at 37° C. for 30 min. Then, the same was washed with phosphate buffered saline (PBS), horseradish peroxidase-labeled SABC complex was added dropwise, and incubated at 37° C. for 20 min. Each step above was washed with PBS. Finally, color development was performed with DAB (color developing is controlled under a microscope) and stained again with hematoxylin, the samples were then dehydrated and sealed. Sections were analyzed by immunohistochemical analysis system of BI-2000 image analysis system. Three sections were collected for endothelial cells of normal arterial vessels and endothelial cells at arterial vulnerable plaques, respectively, and five representative fields were randomly selected. The positive expression of CD44 is as follows: cell membrane and cytoplasm are yellow-brown/chocolate-brown and the background is clear, and the darker the color, the stronger the expression of CD44. The negative expression of CD44 is as follows: no yellow-brown particles are found. The mean absorbance (A) values of positive cells in the endothelial cells of normal arterial vessels and endothelial cells at arterial vulnerable plaques were measured and compared. Results are shown in FIG. 17.

Figure 17:
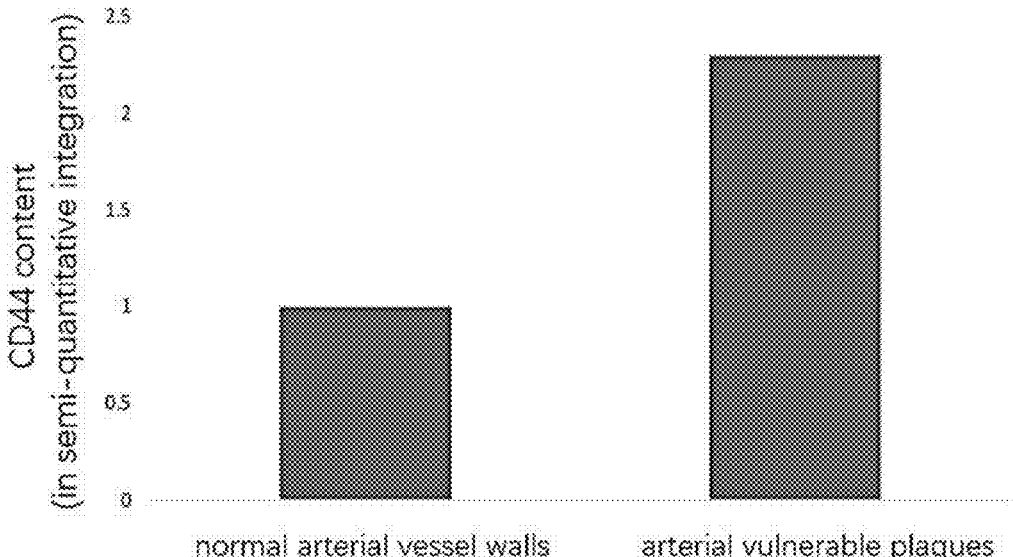
FIG. 17 is a graph showing the determination results (expressed as semi-quantitative integration) of CD44 content on the surface of endothelial cells of normal arterial vessel walls and on the surface of endothelial cells at arterial vulnerable plaques in mice model.

FIG. 17 shows the determination results of CD44 content (in semi-quantitative integration) on the surface of endothelial cells of normal arterial vessel walls and endothelial cells at arterial vulnerable plaques of model mice. As shown in the figure, the CD44 content on the surface of endothelial cells at arterial vulnerable plaques is approximately 2.3 times the CD44 content on the surface of endothelial cells of normal arterial vessels.

2) Comparison of the Affinity of CD44 on the Surface of Endothelial Cells at Arterial Vulnerable Plaques and on the Surface of Endothelial Cells of Normal Arterial Vessel Walls of Mice for Ligand and Antibody Natural ligands for CD44 include: HA, GAG, collagen, laminin, fibronectin, selectin, osteopontin (OPN), and monoclonal antibodies HI44a, HI313, A3D8, H90, IM7, etc.

Endothelial cells at normal arterial vessel walls and endothelial cells at arterial vulnerable plaques of model mice were taken, and the ligand/antibody labeled with amino fluorescein at a concentration of 10 mg/ml was added, the sample was cultured in Dulberic modified Eagle's medium (DMEM) (containing calf serum with a volume fraction of 10%, 100 U/ml penicillin, 100 U/ml streptomycin) at 37° C., in 5% CO2 incubator. After 30 minutes, the mean fluorescence intensity (MFI) was determined by flow cytometry (CytoFLEX, Beckman Coulter, U.S.A.), and the binding force integration of FL-ligand/antibody on the surface of both cells was calculated (the binding force of CD44 of endothelial cells of normal arterial vessel walls to ligand/antibody is set to 1). Results are shown in FIG. 18.

Figure 18:
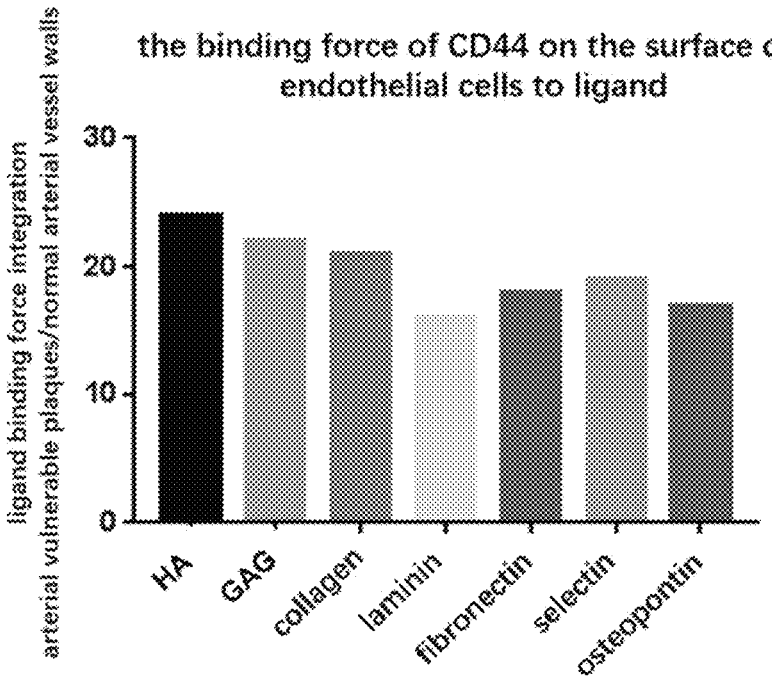
FIG. 18 is a graph showing the determination results (expressed as binding force integration) of the binding force of CD44 on the surface of endothelial cells of normal arterial vessel walls and on the surface of endothelial cells at arterial vulnerable plaques to HA in mice model.
Figure 18:
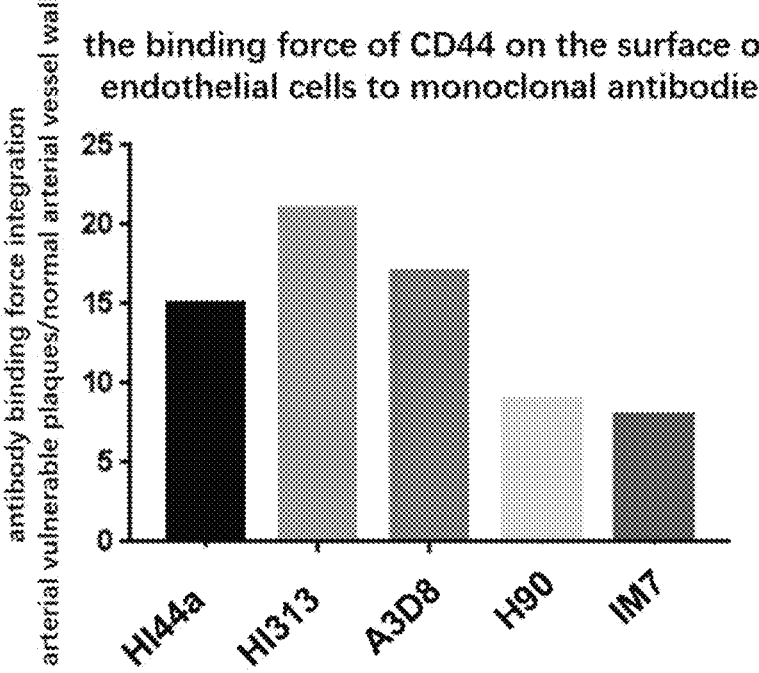

As shown in FIG. 18, the binding force integration of CD44 on the surface of endothelial cells at arterial vulnerable plaques to HA is approximately 24 times that of endothelial cells of normal arterial vessel walls. This indicates that most of the CD44 on the surface of endothelial cells of normal arterial vessel walls are in a static state where it cannot bind to the ligand HA, while the CD44 on the surface of endothelial cells at arterial vulnerable plaques are activated by factors such as inflammatory factors in the internal environment, and the affinity for HA is significantly increased.

Other ligands of CD44 have similar results to HA, and the binding force integration of CD44 on the surface of endothelial cells at vulnerable plaques to GAG is 22 times that of normal cells, and the binding force integration of CD44 on the surface of endothelial cells at vulnerable plaques to collagen is 21 times that of normal cells, the binding force integration of CD44 on the surface of endothelial cells at vulnerable plaques to laminin is 16 times that of normal cells, the binding force integration of CD44 on the surface of endothelial cells at vulnerable plaques to fibronectin is 18 times that of normal cells, the binding force integration of CD44 on the surface of endothelial cells at vulnerable plaques to selectin is 19 times that of normal cells, and the binding force integration of CD44 on the surface of endothelial cells at vulnerable plaques to osteopontin is 17 times that of normal cells.

Similar results were observed for monoclonal antibodies of CD44: the binding force integration of CD44 on the surface of endothelial cells at vulnerable plaques to HI44a is 15 times that of normal cells, the binding force integration of CD44 on the surface of endothelial cells at vulnerable plaques to HI313 is 21 times that of normal cells, the binding force integration of CD44 on the surface of endothelial cells at vulnerable plaques to A3D8 is 17 times that of normal cells, the binding force integration of CD44 on the surface of endothelial cells at vulnerable plaques to H90 is 9 times that of normal cells, and the binding force integration of CD44 on the surface of endothelial cells at vulnerable plaques to IM7 is 8 times that of normal cells.

3) Comparison of the Affinity of CD44 on the Surface of Macrophages Outside the Plaque and That of Macrophages Inside Arterial Vulnerable Plaques for a Ligand/an Antibody Intraperitoneal macrophages and macrophages inside arterial vulnerable plaques of model mice were taken, and the ligand/antibody labeled with amino fluorescein at a concentration of 10 mg/ml was added, the sample was cultured in DMEM (containing calf serum with a volume fraction of 10%, 100 U/ml penicillin, 100 U/ml streptomycin) at 37° C., in 5% $CO_2$ incubator. After 30 minutes, the mean fluorescence intensity (MFI) was determined by flow cytometry (CytoFLEX, Beckman Coulter, U.S.A.), and the binding force integration of FL-HA on the surface of both cells was calculated (the affinity of CD44 on the surface of macrophages outside the plaque for a ligand/an antibody is set to 1). Results are shown in FIG. 19.

Figure 19:
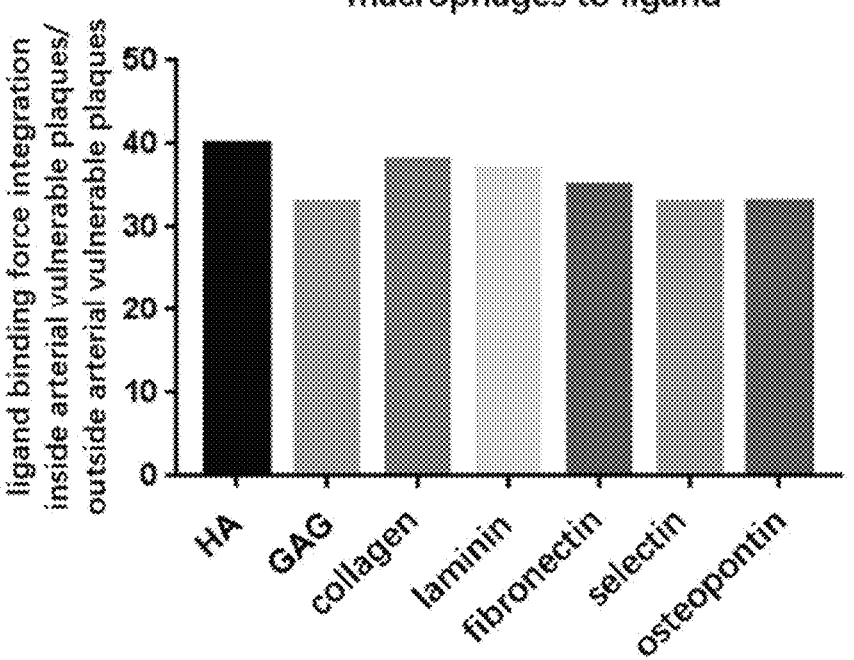
FIG. 19 is a graph showing the determination results (expressed as binding force integration) of the binding force of CD44 on the surface of macrophages outside and inside arterial vulnerable plaques to HA in mice model.
Figure 19:
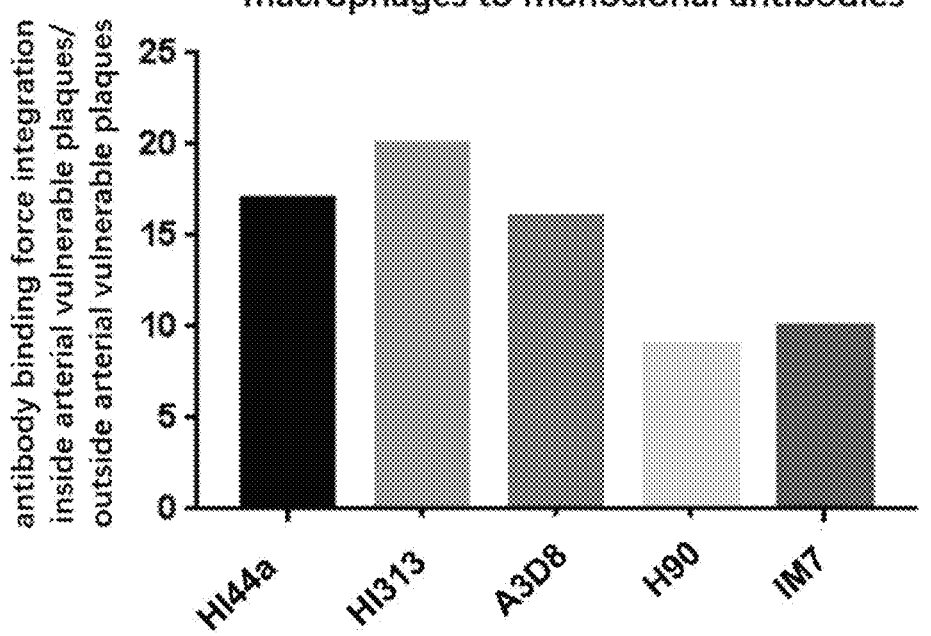

As shown in FIG. 19, the binding force of CD44-HA on the surface of macrophages inside arterial vulnerable plaques is approximately 40 times the binding force of CD44-HA on the surface of macrophages outside the plaques. This indicates that the CD44 on the surface of macrophages inside arterial vulnerable plaques are also activated by factors such as inflammatory factors in the internal environment, and the affinity for HA is significantly increased.

Other ligands of CD44 have similar results to HA, and the binding force integration of CD44 on the surface of macrophages at vulnerable plaques to GAG is 33 times that of normal cells, and the binding force integration of CD44 on the surface of macrophages at vulnerable plaques to collagen is 38 times that of normal cells, the binding force integration of CD44 on the surface of macrophages at vulnerable plaques to laminin is 37 times that of normal cells, the binding force integration of CD44 on the surface of macrophages at vulnerable plaques to fibronectin is 35 times that of normal cells, the binding force integration of CD44 on the surface of macrophages at vulnerable plaques to selectin is 33 times that of normal cells, and the binding force integration of CD44 on the surface of macrophages at vulnerable plaques to osteopontin is 33 times that of normal cells.

Similar results were observed for monoclonal antibodies of CD44: the binding force integration of CD44 on the surface of macrophages at vulnerable plaques to HI44a is 17 times that of normal cells, the binding force integration of CD44 on the surface of macrophages at vulnerable plaques to HI313 is 20 times that of normal cells, the binding force integration of CD44 on the surface of macrophages at vulnerable plaques to A3D8 is 16 times that of normal cells, the binding force integration of CD44 on the surface of macrophages at vulnerable plaques to H90 is 9 times that of normal cells, and the binding force integration of CD44 on the surface of macrophages at vulnerable plaques to IM7 is 10 times that of normal cells.

Based on the results of the above experiments, the following conclusions can be drawn: compared with normal cells (such as endothelial cells of normal arterial vessel walls, macrophages outside the plaque), the density of CD44 on the surface of cells in vulnerable plaques (including endothelial cells, macrophages, etc., which are important for the development of arterial vulnerable plaques) is significantly increased, and its affinity for a ligand is significantly enhanced, thus the specific affinity of CD44 inside arterial vulnerable plaques for a ligand is much higher than that of normal cells, making it very advantageous as an excellent target for the cerasome delivery system of the present invention for targeting vulnerable plaques.

EXPERIMENTAL EXAMPLE 3

In Vivo Experiment about the Effect of the Rosuvastatin Delivery System LP1-(R)-HA, LP1-(R)-SP, LP1-(R)-HA/Tat of the Present Invention on Arterial Vulnerable Plaques Hyaluronic acid (HA) and selectin (SP) are ligands for CD44, which can target vulnerable plaques. Rosuvastatin (R) can reverse plaque, and membrane penetrating peptide (Tat) can increase local penetration and aggregation of drugs. The purpose of this example is to verify the in vivo therapeutic effect of the LP1-(R)-HA, LP1-(R)-SP, LP1-(R)-HA/Tat carrier delivery system described in the present invention on arterial vulnerable plaques.

Experimental Method (1) A normal saline solution of free rosuvastatin was prepared, and the liposome nanocarrier delivery systems loaded with therapeutic agent were prepared by the method described in the above Example 1-3.

(2) Establishment of ApoE−/− mouse model of arterial vulnerable plaque:

SPF-grade ApoE−/− mice (42 mice, 5-6 weeks old, weight 20±1 g) were taken as experimental animals. The mice were fed with an adaptive high-fat diet (fat 10% (w/w), cholesterol 2% (w/w), sodium cholate 0.5% (w/w), and the rest being normal feed for mice) for 4 weeks, and then anaesthetized via intraperitoneal injection of 1% sodium pentobarbital (prepared by adding 1 mg of sodium pentobarbital to 100 ml of normal saline) at a dose of 40 mg/kg. Then, the mice were fixed on the surgical plate in the supine position, disinfected around the neck with 75% (v/v) alcohol, the neck skin was cut longitudinally, and the anterior cervical gland was bluntly separated, and the beating left common carotid artery can be observed on the left side of the trachea. The common carotid artery was carefully separated to the bifurcation. A silicone cannula with a length of 2.5 mm and an inner size of 0.3 mm was placed on the outer periphery of the left common carotid artery. The proximal and distal segments of the cannula were narrowed and fixed by filaments. Local tightening causes rapid blood flow in the proximal end with increased shear force, and thus damage to the intima of the blood vessel. The carotid artery was repositioned and the neck skin was intermittently sutured. All operations were performed under a 10× stereomicroscope. After awakened from the surgery, the mice were returned to the cage, where the ambient temperature was maintained at 20~25° C., and the light was kept under a 12 h/12 h light/dark cycle. At the 4th week after the surgery, lipopolysaccharide (LPS) (1 mg/kg in 0.2 ml phosphate buffered saline, Sigma, U.S.A.) was injected intraperitoneally twice a week for 10 weeks to induce chronic inflammation. At the 8th week after the surgery, mice were placed in a 50 ml syringe (sufficient vents reserved) to trigger restrictive mental stress, 6 hours/day, 5 days per week for a total of 6 weeks. The mouse model of atherosclerotic vulnerable plaque was completed at the 14th week after the surgery.

(3) Grouping and treatment of experimental animals:

The experimental animals were randomly divided into the following groups, 6 mice in each group:

control group of vulnerable plaque model: this group of animals do not undergo any therapeutic treatment;

group intragastrically administered with rosuvastatin: treatment by intragastric administration at a dose of 10 mg rosuvastatin per kg body weight;

group intravenously administered with rosuvastatin: treatment by intravenous administration at a dose of 0.66 mg rosuvastatin per kg body weight;

LP1-(R)-HA group: treatment by intravenous administration at a dose of 0.66 mg rosuvastatin per kg body weight;

LP1-(R)-SP group: treatment by intravenous administration at a dose of 0.66 mg rosuvastatin per kg body weight;

LP1-(R)-HA/Tat group: treatment by intravenous administration at a dose of 0.66 mg rosuvastatin per kg body weight;

Except for the control group of vulnerable plaque model, the treatment group was treated once every other day for a total of 5 treatments. For animals in each group, carotid MRI scans were performed before and after treatment to detect plaque and lumen area, and the percentage of plaque progression was calculated.

Percentage of plaque progression=(plaque area after treatment−plaque area before treatment)/lumen area.

Experimental Results

Figure 20:
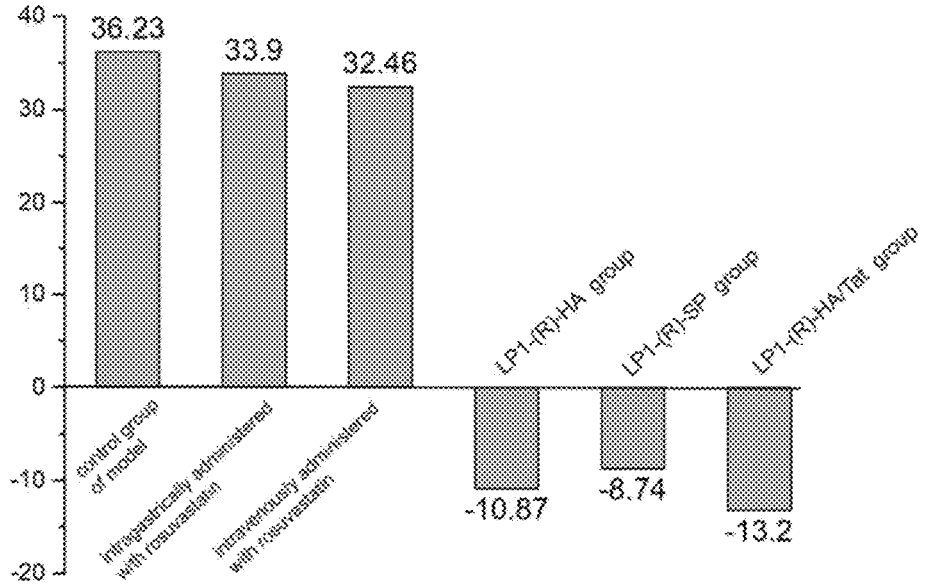
FIG. 20 is a graph showing the therapeutic effect of LP1-(R)-HA, LP1-(R)-SP, LP1-(R)-HA/Tat nano delivery system of the present invention on carotid vulnerable plaque in mice model.

FIG. 20 displays the in vivo therapeutic effect of the carrier delivery system LP1-(R)-HA, LP1-(R)-SP, LP1-(R)-HA/Tat of the present invention on arterial vulnerable plaques. As shown in the figure, during the high-fat diet feeding (10 days), the atherosclerosis of the control group (without any treatment) progressed by 36.23%. Intragastric administration of rosuvastatin can delay the progression of plaque, but it is also progressed by 33.9%. Intravenous administration of rosuvastatin also delayed plaque progression, but it also progressed by 32.46%. However, targeted nano drug delivery therapy significantly inhibited the progress of plaque, and even reversed and subsided the plaque volume. LP1-(R)-HA group eliminated the plaque by 10.87%, LP1-(R)-SP eliminated the plaque by 8.74%, and LP1-(R)-HA/Tat group eliminated the plaque by 13.2%.

To sum up, free rosuvastatin has a certain therapeutic effect on arterial vulnerable plaque in mice, whether given by intragastric administration or intravenous administration, but it cannot prevent vulnerable plaque from continuing to grow. However, when rosuvastatin is formulated in the nano delivery system of the present invention, the therapeutic effect on vulnerable plaque is significantly improved, and the therapeutic effect of reversing plaque growth (narrowing plaque) is achieved, and the nano system with functional modification has better effect.

EXPERIMENTAL EXAMPLE 4

In Vivo Experiment about the Effect of the Delivery System LP2-(At)-HA, LP2-(At)-SEP/IM7, LP2-(At/miRNA-33a)-IM7 of the Present Invention on Arterial Vulnerable Plaques Hyaluronic acid (HA) and IM7 are ligands for CD44, which can target vulnerable plaques. Atorvastatin (At) can reverse plaque, self peptide (SEP) can increase local penetration and aggregation of drugs, and miRNA-33a can increase cholesterol efflux. The purpose of this example is to verify the in vivo therapeutic effect of the LP2-(At)-HA, LP2-(At)-SEP/IM7, LP2-(At/miRNA-33a)-IM7 carrier delivery system described in the present invention on arterial vulnerable plaques.

Experimental Method (1) A normal saline solution of free atorvastatin was prepared, and the liposome nanocarrier delivery systems loaded with therapeutic agent were prepared by the method described in the above example 4-6.

(2) Establishment of ApoE−/− mouse model of arterial vulnerable plaque according to Experimental Example 4.

(3) Grouping and treatment of experimental animals:

The experimental animals were randomly divided into the following groups, 6 mice in each group:

control group of vulnerable plaque model: this group of animals do not undergo any therapeutic treatment;

group intragastrically administered with atorvastatin: treatment by intragastric administration at a dose of 20 mg atorvastatin per kg body weight;

group intravenously administered with atorvastatin: treatment by intravenous administration at a dose of 1.2 mg atorvastatin per kg body weight;

PEG-free LP2-(At)-HA group: treatment by intravenous administration at a dose of 1.2 mg atorvastatin per kg body weight;

LP2-(At)-HA group: treatment by intravenous administration at a dose of 1.2 mg atorvastatin per kg body weight;

LP2-(At)-IM7 group: treatment by intravenous administration at a dose of 1.2 mg atorvastatin per kg body weight;

LP2-(At)-SEP/IM7 group: treatment by intravenous administration at a dose of 1.2 mg atorvastatin per kg body weight;

LP2-(At/miRNA-33a)-IM7 group: treatment by intravenous administration at a dose of 1.2 mg atorvastatin per kg body weight;

Except for the control group of vulnerable plaque model, the treatment group was treated once every other day for a total of 5 treatments. For animals in each group, carotid MRI scans were performed before and after treatment to detect plaque and lumen area, and the percentage of plaque progression was calculated.

Percentage of plaque progression=(plaque area after treatment−plaque area before treatment)/lumen area.

Experimental Results

Figure 21:
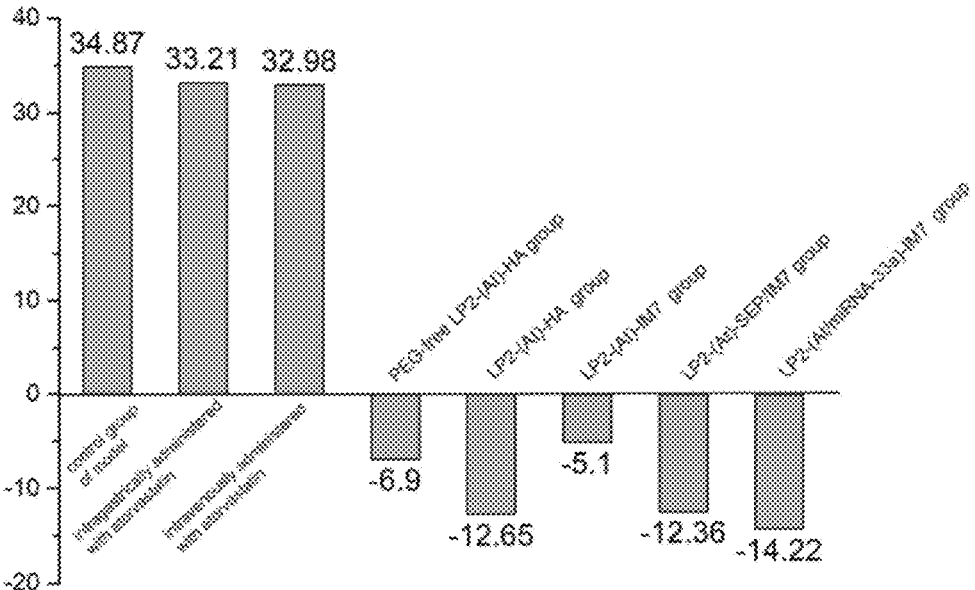
FIG. 21 is a graph showing the therapeutic effect of LP2-(At)-HA, LP2-(At)-SEP/IM7, LP2-(At/miRNA-33a)-IM7 nano delivery system of the present invention on carotid vulnerable plaque in mice model.

FIG. 21 displays the in vivo therapeutic effect of the carrier delivery system LP2-(At)-HA, LP2-(At)-SEP/IM7, LP2-(At/miRNA-33a)-IM7 of the present invention on arterial vulnerable plaques. As shown in the figure, during the high-fat diet feeding (10 days), the atherosclerosis of the control group (without any treatment) progressed by 34.87%. Intragastric administration of atorvastatin can delay the progression of plaque, but it is also progressed by 33.21%. Intravenous administration of atorvastatin also delayed plaque progression, but it also progressed by 32.98%. However, targeted nano drug delivery therapy significantly inhibited the progress of plaque, and even reversed and subsided the plaque volume. PEG-free LP2-(At)-HA group eliminated the plaque by 6.9%, LP2-(At)-HA group eliminated the plaque by 12.65%, LP2-(At)-IM7 eliminated the plaque by 5.1%, LP2-(At)-SEP/IM7 eliminated the plaque by 12.43%, and LP2-(At/miRNA-33a)-IM7t group eliminated the plaque by 14.22%.

To sum up, free atorvastatin has a certain therapeutic effect on arterial vulnerable plaque in mice, whether given by intragastric administration or intravenous administration, but it cannot prevent vulnerable plaque from continuing to grow. However, when atorvastatin is formulated in the liposome nanocarrier delivery system of the present invention, the therapeutic effect on vulnerable plaque is significantly improved, and the therapeutic effect of reversing plaque growth (narrowing plaque) is achieved, and the nano system with PEG or SEP functional modification has better effect, and the nanocarrier loaded with statins and nucleic acid has significant effect.

EXPERIMENTAL EXAMPLE 5

In Vivo Experiment about the Effect of the Delivery System LP2-(AuNP/R)-OPN of the Present Invention on Arterial Vulnerable Plaques (Dual Function of CT Tracing and Therapy)

Osteopontin (OPN) is a ligand for CD44, which can target vulnerable plaques. Rosuvastatin (R) can reverse plaque, and nanogold (Au NP) is a CT tracer. The purpose of this example is to verify the in vivo tracing and therapeutic effect of the nanocarrier delivery system loaded with CT tracer and rosuvastatin described in the present invention on arterial vulnerable plaques.

Experimental Method (1) A normal saline solution of free rosuvastatin was prepared, and the liposome nano delivery systems loaded with CT tracer and therapeutic agent was prepared by the method described in the above Example 7.

(2) Establishment of ApoE−/− mouse model of arterial vulnerable plaque according to Experimental Example 4.

(3) Trace of vulnerable plaque in experimental animals:

The experimental animals were randomly divided into the following groups, 6 mice in each group:

Free nanogold group: the dosage of nanogold was 0.1 mg/kg body weight;

LP2-(AuNP/R)-OPN group: the dosage of nanogold was 0.1 mg/kg body weight;

LP2-(iopromide)-OPN group: the dosage of iopromide was 0.1 mg/kg body weight;

LP2-(iodixanol)-OPN group: the dosage of iodixanol was 0.1 mg/kg body weight;

LP2-(iodofluoroalcohol)-OPN group: the dosage of iodofluoroalcohol was 0.1 mg/kg body weight.

Animals in each experimental group were injected with the corresponding tracer through the tail vein, and CT imaging was performed before administration and 2 hours after administration to observe the identification of atherosclerotic vulnerable plaque in each group.

(4) Grouping and treatment of experimental animals:

The experimental animals were randomly divided into the following groups, 6 mice in each group:

control group of vulnerable plaque model: this group of animals do not undergo any therapeutic treatment;

group intragastrically administered with rosuvastatin: treatment by intragastric administration at a dose of 10 mg rosuvastatin per kg body weight;

group intravenously administered with rosuvastatin: treatment by intravenous administration at a dose of 0.67 mg rosuvastatin per kg body weight;

LP2-(AuNP/R)-OPN group: treatment by intravenous administration at a dose of 0.67 mg rosuvastatin per kg body weight;

Except for the control group of vulnerable plaque model, the treatment group was treated once every other day for a total of 5 treatments. For animals in each group, carotid MRI scans were performed before and after treatment to detect plaque and lumen area, and the percentage of plaque progression was calculated.

Percentage of plaque progression=(plaque area after treatment−plaque area before treatment)/lumen area.

Experimental Results

Figure 22:
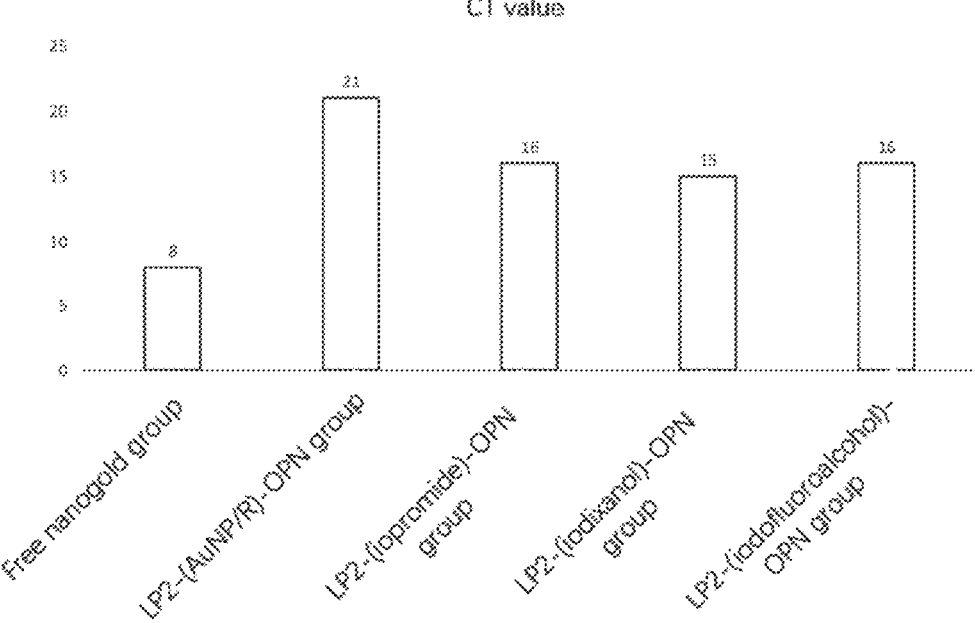
FIG. 22 is a graph showing the in vivo tracing effect of LP2-(AuNP/R)-OPN and other CT tracer nano delivery system of the present invention on carotid vulnerable plaques in mice model.

FIG. 22 displays the in vivo tracing effect of the liposome delivery system of the present invention loaded with a tracer on arterial vulnerable plaques. As shown in the figure, the free nanogold particles show a certain tracing effect on arterial vulnerable plaques in mice. Compared with the free nanogold particles, when the nanogold, iopromide, iodixanol, iodofluoroalcohol are formulated in a targeting liposome delivery system, the tracing effect on vulnerable plaques has been improved significantly. In summary, administration in the liposome delivery system of the present invention whose surface is modified with a targeting ligand can significantly improve the recognition effect of the nanogold on vulnerable plaques compared to the administration of the free nanogold particles, resulting in better tracing effect.

Figure 23:
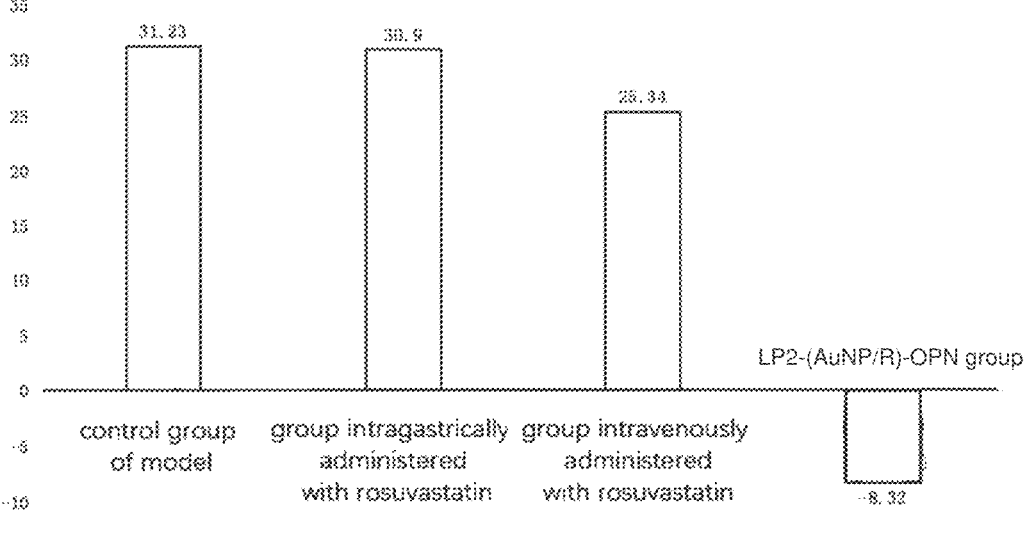
FIG. 23 is a graph showing the therapeutic effect of the LP2-(AuNP/R)-OPN nano delivery system of the present invention on carotid vulnerable plaques in mice model.

FIG. 23 displays the in vivo therapeutic effect of the carrier delivery system LP2-(AuNP/R)-OPN of the present invention on arterial vulnerable plaques. As shown in the figure, during the high-fat diet feeding (10 days), the atherosclerosis of the control group (without any treatment) progressed by 31.23%. Intragastric administration of rosuvastatin can delay the progression of plaque, but it is also progressed by 30.9%. Intravenous administration of rosuvastatin also delayed plaque progression, but it also progressed by 25.34%. However, targeted nano drug delivery therapy significantly inhibited the progress of plaque, and even reversed and subsided the plaque volume. LP2-(AuNP/R)-OPN group eliminated the plaque by 8.32%.

To sum up, free rosuvastatin has a certain therapeutic effect on arterial vulnerable plaque in mice, whether given by intragastric administration or intravenous administration, but it cannot prevent vulnerable plaque from continuing to grow. However, when rosuvastatin and nanogold are formulated in the nano delivery system of the present invention, the diagnostic and therapeutic effect on vulnerable plaque is significantly improved, and plays an early warning role for high-risk patients, and the therapeutic effect of reversing plaque growth (narrowing plaque) is achieved.

EXPERIMENTAL EXAMPLE 6

In Vivo Tracing Experiment about the Effect of the Delivery System LP1-(Fe3O4/DXMS)-HI44a, LP1-(Fe3O4/IL-10)-HI44a of the Present Invention on Arterial Vulnerable Plaques (MRI Tracing) and Anti-Inflammatory Treatment Monoclonal antibody (HI44a) is a ligand for CD44, which can target vulnerable plaques. Dexamethasone (DXMS) has anti-inflammatory and plaque progression inhibiting effects, and Fe3O4 is a MRI tracer. The purpose of this example is to verify the in vivo tracing and therapeutic effect of the nanocarrier delivery system loaded with MRI tracer and dexamethasone described in the present invention on arterial vulnerable plaques. In addition, gadoterate meglumine, gadodiamide and gadopentetic acid can also be prepared into nano-preparations, showing targeted MRI tracing effect.

(1) The liposome nano delivery systems loaded with MRI tracer and therapeutic agent was prepared by the method described in the above Example 8-9.

(2) Establishment of ApoE−/− mouse model of arterial vulnerable plaque according to Experimental Example 4.

(3) Trace of vulnerable plaque in experimental animals:

The experimental animals were randomly divided into the following groups, 6 mice in each group:

Free Fe3O4 group: the dosage of Fe3O4 was 0.1 mg/kg body weight;

LP1-(Fe3O4/DXMS)-HI44a group: the dosage of Fe3O4 was 0.1 mg/kg body weight;

LP1-(Fe3O4/IL-10)-HI44a group: the dosage of Fe3O4 was 0.1 mg/kg body weight;

LP1-(gadoterate meglumine)-HI44a group: the dosage of gadoterate meglumine was 0.1 mg/kg body weight;

LP1-(gadodiamide)-HI44a group: the dosage of gadodiamide was 0.1 mg/kg body weight;

LP1-(gadopentetic acid)-HI44a group: the dosage of gadopentetic acid was 0.1 mg/kg body weight.

Animals in each experimental group were injected with the corresponding tracer through the tail vein, and MRI imaging was performed before administration and 2 hours after administration to observe the identification of atherosclerotic vulnerable plaque in each group.

(4) Grouping and treatment of experimental animals:

The experimental animals were randomly divided into the following groups, 6 mice in each group:

control group of vulnerable plaque model: this group of animals do not undergo any therapeutic treatment;

LP1-(Fe3O4/DXMS)-HI44a group: treatment by intravenous administration at a dose of 0.1 mg dexamethasone per kg body weight;

LP1-(Fe3O4/IL-10)-HI44a group: treatment by intravenous administration at a dose of 0.1 μmol IL-10 per kg body weight;

Except for the control group of vulnerable plaque model, the treatment group was treated once every other day for a total of 5 treatments. For animals in each group, carotid MRI scans were performed before and after treatment to detect plaque and lumen area, and the percentage of plaque progression was calculated.

Percentage of plaque progression=(plaque area after treatment−plaque area before treatment)/lumen area.

Experimental Results

Figure 24:
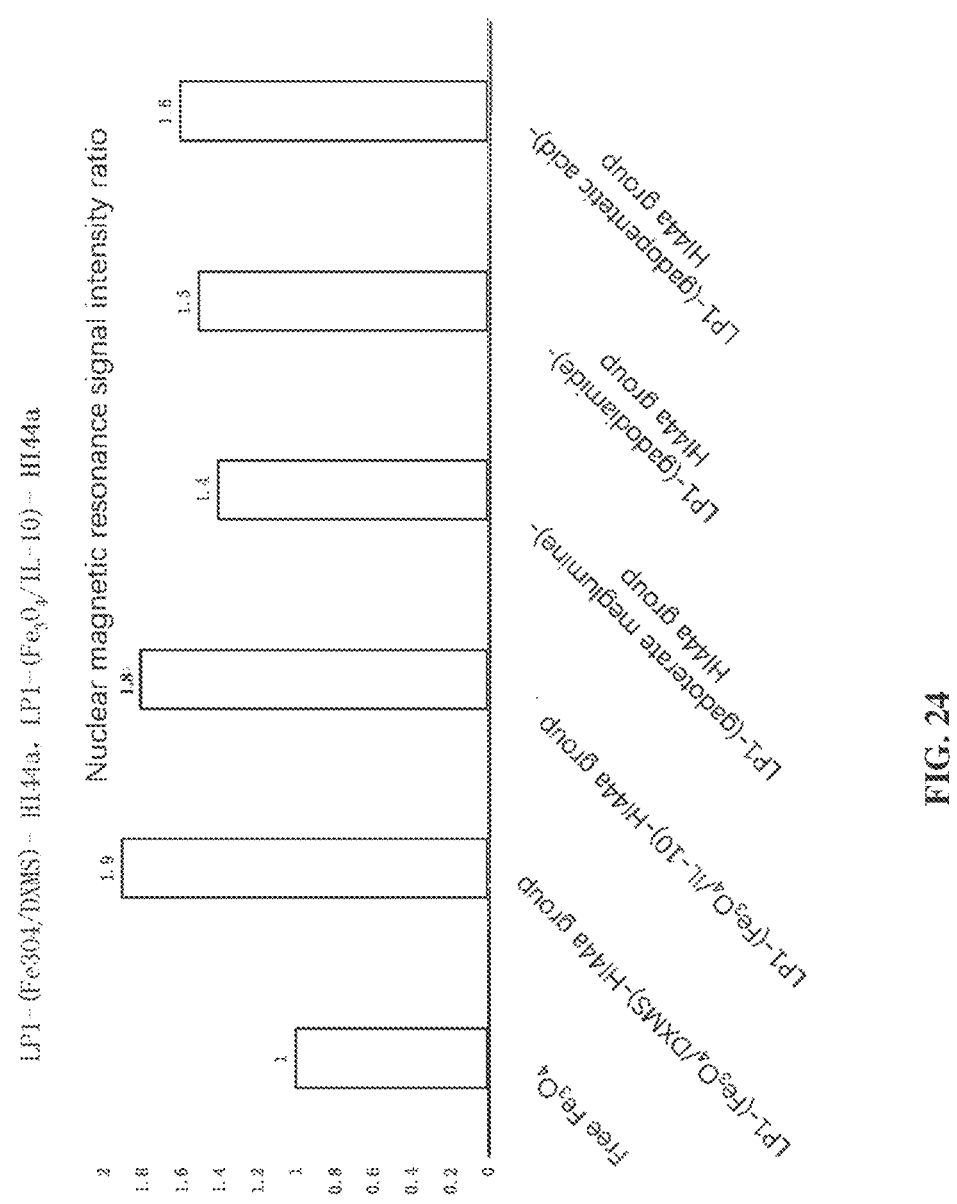
FIG. 24 is a graph showing the in vivo tracing effect of LP1-(Fe₃O₄/DXMS)-HI44a, LP1-(Fe₃O₄/IL-10)-HI44a and other MRI tracer nano delivery system of the present invention on carotid vulnerable plaques in mice model.

FIG. 24 displays the in vivo tracing effect of the liposome delivery system of the present invention loaded with a tracer on arterial vulnerable plaques. As shown in the figure, the free Fe3O4 particles show a certain tracing effect on arterial vulnerable plaques in mice. Compared with the free Fe3O4 particles, when the Fe3O4 is formulated in a targeting liposome delivery system, the tracing effect on vulnerable plaques has been improved very significantly. Using other MRI nano contrast agents, the tracing effect of vulnerable plaque is also very good. In summary, administration in the liposome delivery system of the present invention whose surface is modified with a targeting ligand can significantly improve the recognition effect of the nanogold on vulnerable plaques compared to the administration of the free MRI tracer, resulting in better tracing effect.

Figure 25:
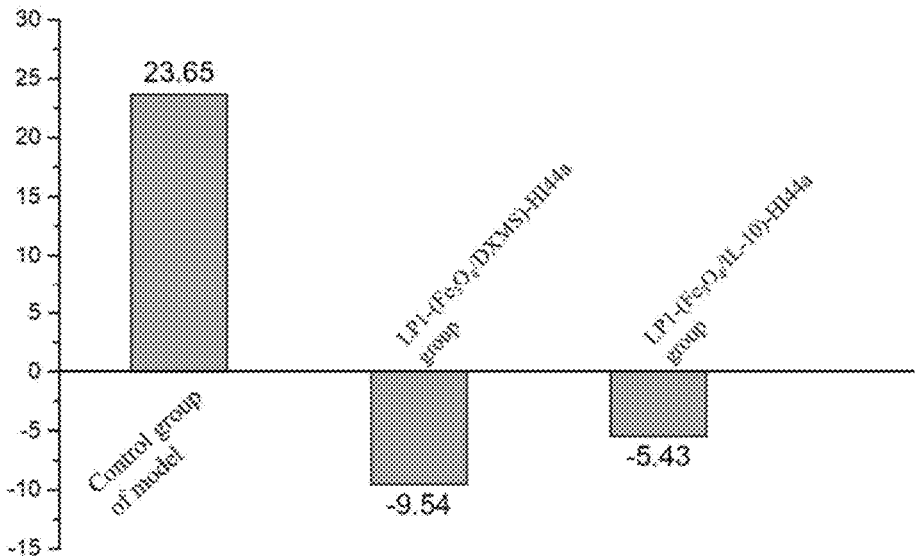
FIG. 25 is a graph showing the therapeutic effect of the LP1-(Fe₃O₄/DXMS)-HI44a, LP1-(Fe₃O₄/IL-10)-HI44a nano delivery system of the present invention on carotid vulnerable plaques in mice model.

FIG. 25 displays the in vivo therapeutic effect of the carrier delivery system LP1-(Fe3O4/DXMS)-HI44a and LP1-(Fe3O4/IL-10)-HI44a of the present invention on arterial vulnerable plaques. As shown in the figure, during the high-fat diet feeding (10 days), the atherosclerosis of the control group (without any treatment) progressed by 23.65%. However, targeted nano drug delivery therapy significantly inhibited the progress of plaque, and even reversed and subsided the plaque volume. LP1-(Fe3O4/DXMS)-HI44a group eliminated the plaque by 9.54%. LP1-(Fe3O4/IL-10)-HI44a group eliminated the plaque by 5.43%.

To sum up, for the arterial vulnerable plaque in mice, when dexamethasone or IL-10 are formulated in the nano delivery system of the present invention, the diagnostic and therapeutic effect on vulnerable plaque is significantly improved, and plays an early warning role for high-risk patients, and the therapeutic effect of reversing plaque growth (narrowing plaque) is achieved. Loading Fe3O4 simultaneously can achieve MRI imaging and real-time monitoring of the disease.

EXPERIMENTAL EXAMPLE 7

In Vivo Experiment about the Effect of the Delivery System LP1-(Asp/Clo)-Col of the Present Invention on Arterial Vulnerable Plaques Aspirin (Asp) and clopidogrel (Clo) are antiplatelet drugs, which can reduce platelet aggregation and mortality from cardiovascular events. The purpose of this example is to verify the in vivo therapeutic effect of the LP1-(Asp/Clo)-Col carrier delivery system described in the present invention on arterial vulnerable plaques.

Experimental Method (1) Normal saline solution of free aspirin and clopidogrel was prepared, and the liposome nanocarrier delivery systems loaded with therapeutic agent was prepared by the method described in the above Example 10.
(2) Establishment of ApoE−/− mouse model of arterial vulnerable plaque: The ApoE−/− mice were fed with high-fat diet for 30 weeks to form atherosclerotic plaques in their systemic arteries, and snake venom was given to induce rupture of vulnerable plaques to form acute coronary syndrome.
(3) Grouping and treatment of experimental animals:
The experimental animals were randomly divided into the following groups, 10 mice in each group:
control group of vulnerable plaque model: this group of animals do not undergo any therapeutic treatment;
group intragastrically administered with aspirin and clopidogrel: treatment by intragastric administration at a dose of 100 mg aspirin per kg body weight and 75 mg clopidogrel per kg body weight;
LP1-(Asp/Clo)-Col group: treatment by intravenous administration a at a dose of 10 mg aspirin per kg body weight and 7.5 mg clopidogrel per kg body weight.
Except for the control group of vulnerable plaque model, the treatment group was treated once every other day for a total of 5 treatments. For animals in each group, the mortality rate of mice in a month was observed, and the bleeding time (BT) of mice was detected by tail amputation.

Experimental Results

Figure 26:
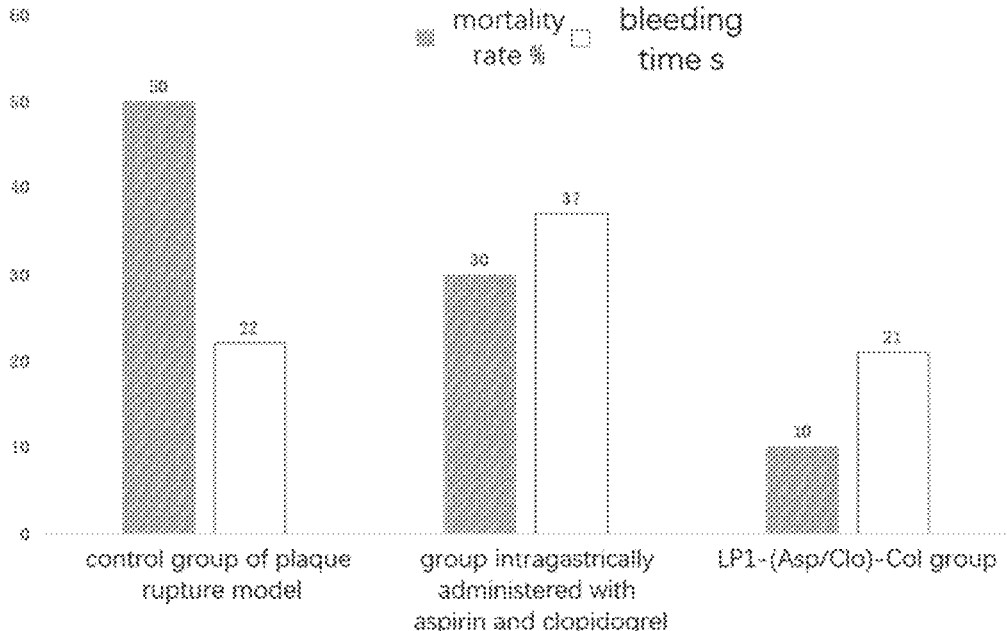
FIG. 26 is a graph showing the therapeutic effect of the LP1-(Asp/Clo)-Col nano delivery system of the present invention on rupture of vulnerable arterial plaques in mice model.

FIG. 26 displays the in vivo therapeutic effect of the carrier delivery system LP1-(Asp/Clo)-Col of the present invention on arterial vulnerable plaques. As shown in the figure, the mortality rate of mice in the control group (without any treatment) was 50%. Intragastric administration of aspirin and clopidogrel can reduce the mortality rate to 30%. LP1-(Asp/Clo)-Col therapy can reduce the mortality rate to 10%. From the point of bleeding time, LP1-(Asp/Clo)-Col group did not significantly extend, while intragastric administration of aspirin and clopidogrel significantly prolonged bleeding time in mice.

To sum up, for animals with vulnerable plaque rupture, oral dual antiplatelet therapy can reduce the mortality rate, but prolong bleeding time and increase bleeding risk. However, the loading of antiplatelet drugs into the nano delivery system has better effect than oral drugs and does not increase bleeding risk.

EXPERIMENTAL EXAMPLE 8

In Vivo Experiment about the Effect of the Delivery System LP1-(F-FDG)-OPN of the Present Invention on Arterial Vulnerable Plaques Osteopontin (OPN) is a ligand for CD44, which can target vulnerable plaques. Rosuvastatin (R) can reverse plaque, and fluorine 18 (18F)-labeled fludeoxyglucose (F-FDG) is a radioisotopic tracer. The purpose of this example is to verify the in vivo tracing and therapeutic effect of the liposome nanocarrier delivery system loaded with radioisotopic tracer described in the present invention on arterial vulnerable plaques.

Experimental Method (1) A normal saline solution of free rosuvastatin was prepared, and the liposome nano delivery systems loaded with radioisotopic tracer and therapeutic agent was prepared by the method described in the above Example 11.
(2) Establishment of ApoE−/− mouse model of arterial vulnerable plaque according to Experimental Example 4.
(3) Trace of vulnerable plaque in experimental animals:
The experimental animals were randomly divided into the following groups, 6 mice in each group:
Free F-FDG group: the dosage of F-FDG was 2 mSv/kg body weight;
LP1-(F-FDG)-OPN group: the dosage of F-FDG was 2 mSv/kg body weight;
LP1-(99mTc)-OPN group: the dosage of 99mTc was 2 mSv/kg body weight;
LP1-(I-131)-OPN group: the dosage of 1-131 was 2 mSv/kg body weight.
Animals in each experimental group were injected with the corresponding tracer through the tail vein, and radioisotopic imaging was performed before administration and 2 hours after administration to observe the identification of atherosclerotic vulnerable plaque in each group.

Experimental Results

Figure 27:
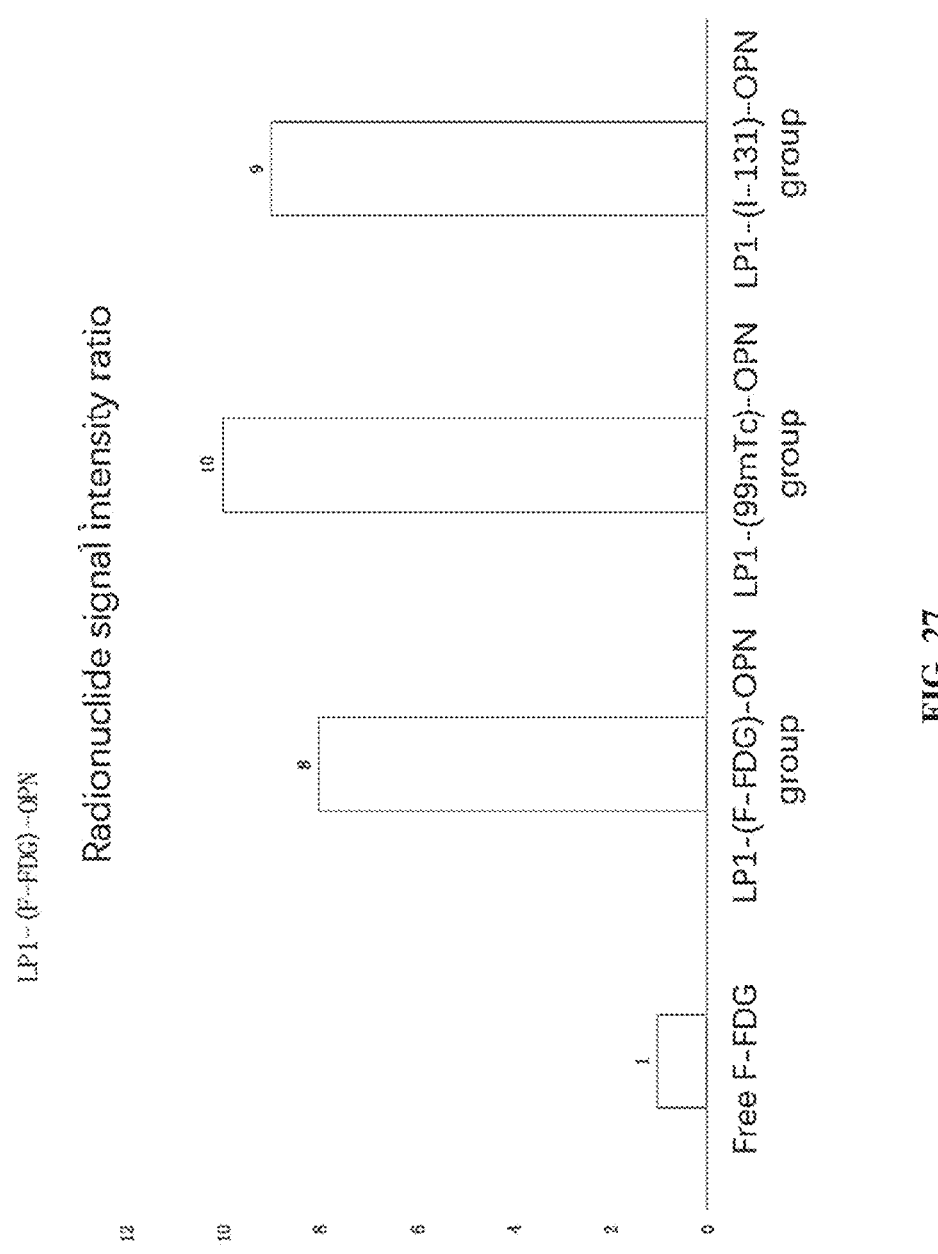
FIG. 27 is a graph showing the in vivo tracing effect of the radioisotopic tracer LP1-(F-FDG)-OPN nano delivery system of the present invention on carotid vulnerable plaques in mice model.

FIG. 27 displays the in vivo tracing effect of the liposome delivery system of the present invention loaded with radioisotopic tracer on arterial vulnerable plaques. As shown in the figure, the free F-FDG doesn't show any tracing effect on arterial vulnerable plaques in mice. When the F-FDG, Technetium 99 (99mTc), Iodine 131 (I-131) is formulated in a targeting liposome delivery system, the tracing effect on vulnerable plaques has been improved very significantly. In summary, administration in the liposome delivery system of the present invention whose surface is modified with a targeting ligand can significantly improve the recognition effect of the nanogold on vulnerable plaques compared to the free F-FDG, resulting in better tracing effect.

The various aspects of the invention have been exemplified by the above-described embodiments. It is apparent that the above-described embodiments are merely illustrative of the examples, and are not intended to limit the embodiments. Other variations or modifications of the various forms may be made by those skilled in the art in light of the above description. There is no need and no way to exhaust all of the implementations. Obvious changes or variations resulting therefrom are still within the scope of the invention.

The invention claimed is:

1. A liposome nanocarrier delivery system, characterized in that the surface of the nanocarrier is partially modified by a targeting ligand;

wherein the targeting ligand is a hyaluronic acid, a pharmaceutically acceptable salt of the hyaluronic acid, or a C1 to C6 alkyl ester of the hyaluronic acid;

wherein the hyaluronic acid, pharmaceutically acceptable salt of the hyaluronic acid, or C1 to C6 alkyl ester of the hyaluronic acid has a molecular weight in the range of 1-20 KDa;

wherein the nanocarrier further comprises a long-chain phospholipid and cholesterol; and wherein the nanocarrier is loaded with rosuvastatin, or a pharmaceutically acceptable salt thereof.

2. The liposome nanocarrier delivery system according to claim 1, characterized in that, the nanocarrier is further loaded with a CD44 activator.

3. A medicament, characterized in that the medicament comprises the liposome nanocarrier delivery system of claim 1 and a pharmaceutically acceptable carrier.

4. The liposome nanocarrier delivery system according to claim 2, wherein the CD44 activator is a CD44 monoclonal antibody, ILS, IL12, IL18, TNF-α, or LPS.

5. The liposome nanocarrier delivery system according to claim 1, wherein the surface of the nanocarrier is further modified with one or more selected from the group consisting of PEG, membrane penetrating peptide, and self peptide.

6. The liposome nanocarrier delivery system according to claim 1, wherein the targeting ligand is a hyaluronic acid.

7. The liposome nanocarrier delivery system of claim 1, wherein the surface of the nanocarrier is further modified with PEG.

8. The liposome nanocarrier delivery system of claim 1, wherein the nanocarrier is loaded with rosuvastatin.

9. The liposome nanocarrier delivery system according to claim 1, wherein the hyaluronic acid, pharmaceutically acceptable salt of the hyaluronic acid, or C1 to C6 alkyl ester of the hyaluronic acid has a molecular weight in the range of 2-10 KDa.

10. The liposome nanocarrier delivery system according to claim 1, wherein the hyaluronic acid, pharmaceutically acceptable salt of the hyaluronic acid, or C1 to C6 alkyl ester of the hyaluronic acid has a molecular weight of 10 KDa.

11. The liposome nanocarrier delivery system according to claim 1, wherein the targeting ligand is a hyaluronic acid; and the hyaluronic acid has a molecular weight in the range of 2-10 KDa.

12. The liposome nanocarrier delivery system according to claim 11, wherein the hyaluronic acid has a molecular weight of 10 KDa.

13. The liposome nanocarrier delivery system according to claim 6, wherein the surface of the nanocarrier is further modified with PEG.

14. The liposome nanocarrier delivery system according to claim 11, wherein the surface of the nanocarrier is further modified with PEG.

15. The liposome nanocarrier delivery system according to claim 6, wherein the surface of the nanocarrier is further modified with a membrane penetrating peptide.

16. The liposome nanocarrier delivery system according to claim 6, wherein the liposome nanocarrier is a small unilamellar vesicle, a large unilamellar vesicle, or a multi-lamellar vesicle.

17. The liposome nanocarrier delivery system according to claim 14, wherein the surface of the nanocarrier is further modified with a membrane penetrating peptide.

18. The liposome nanocarrier delivery system according to claim 12, wherein the surface of the nanocarrier is further modified with PEG.

19. The liposome nanocarrier delivery system according to claim 18, wherein the surface of the nanocarrier is further modified with a membrane penetrating peptide.

* * * * *